US012578332B2

(12) United States Patent
Woller

(10) Patent No.: US 12,578,332 B2
(45) Date of Patent: Mar. 17, 2026

(54) TCR-INDEPENDENT MOLECULAR IDENTIFICATION OF MUTATION-RELATED AND TUMOR-SPECIFIC T CELLS

(71) Applicant: MEDIZINISCHE HOCHSCHULE HANNOVER, Hannover (DE)

(72) Inventor: Norman Woller, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 1004 days.

(21) Appl. No.: 17/754,452

(22) PCT Filed: Oct. 15, 2020

(86) PCT No.: PCT/EP2020/079038
§ 371 (c)(1),
(2) Date: Apr. 1, 2022

(87) PCT Pub. No.: WO2021/074291
PCT Pub. Date: Apr. 22, 2021

(65) Prior Publication Data
US 2022/0357324 A1 Nov. 10, 2022

(30) Foreign Application Priority Data
Oct. 16, 2019 (EP) ..................................... 19203651

(51) Int. Cl.
*G01N 33/569* (2006.01)

(52) U.S. Cl.
CPC ................. *G01N 33/56972* (2013.01); *G01N 33/56966* (2013.01); *G01N 2333/70517* (2013.01); *G01N 2333/70553* (2013.01)

(58) Field of Classification Search
CPC ....... G01N 33/56966; G01N 33/56972; G01N 33/574; G01N 33/57492; G01N 2333/70517; G01N 2333/70553; G01N 2333/70596
See application file for complete search history.

(56) References Cited

U.S. PATENT DOCUMENTS

2020/0149009 A1* 5/2020 Regev ................. A61K 40/4254
2022/0152176 A1* 5/2022 Srinivasan ........... C12Q 1/6886

FOREIGN PATENT DOCUMENTS

WO 2013/126809 A1 8/2013
WO 2019/014581 A1 1/2019
WO 2019/053244 A1 3/2019

OTHER PUBLICATIONS

Ostroumov, Dmitrij, et al., "CD4 and CD8 T lymphocyte interplay in controlling tumor growth," Cell. Mol. Life Sci. vol. 75 (2018), pp. 689-713.

Dunn, Gavin P., et al., "The Three Es of Cancer Immunoediting," Annu. Rev. Immunol. vol. 22 (2004), pp. 329-360.
Dudley, Mark E., et al., "Cancer Regression and Autoimmunity in Patients After Clonal Repopulation with Antitumor Lymphocytes," NIH Public Access, Science (2007) (10 pages).
Knocke, Sarah, et al., "Tailored Tumor Immunogenicity Reveals Regulation of CD4 and CD8 T Cell Responses against Cancer," Cell Reports, vol. 17 (2016), pp. 2234-2246.
Rai, Deepa, et al., "Tracking the Total CD8 T Cell Response to Infection Reveals Substantial Discordance in Magnitude and Kinetics between Inbred and Outbred Hosts," The Journal of Immunology, vol. 183 (2009), pp. 7672-7681.
Castle, John C., et al., "Exploiting the Mutanome for Tumor Vaccination," Cancer Research, vol. 72, No. 5 (2012), pp. 1081-1091.
Van Rooij, Nienke, et al., "Tumor Exome Analysis Reveals Neoantigen-Specific T-Cell Reactivity in an Ipilimumab-Responsive Melanoma," J. Clin. Oncol., vol. 31 (2013) (8 pages).
Garcia-Guerrero, Estefania, et al., Selection of Tumor-Specific Cytotoxic T. Lymphocytes in Acute Myeloid Leukemia Patients Through the Identification of T-Cells Capable to Establish Stable Interactions With the Leukemic Cells: "Doublet Technology", Frontiers in Immunolgy, vol. 9 (2018) (15 pages).
Huang, Alexander C., et al., "T-cell invigoration to tumour burden ratio associated with anti-PD-1 response," HHS Public Access, Nature (2017) (27 pages).
Tsai, Yien Che, et al., "Dissecting the Deverse Functions of the Metastasis Suppressor CD82/KAI1," FEBS Lett. vol. 585 (2011) (16 pages).
Gubin, Matthew M., et al., "Checkpoint Blockade Cancer Immunotherapy Targets Tumour-Specific Mutant Antigens," Nature, vol. 515 (2014) (32 pages).
Champiat, Stéphane, et al., "Hyperprogressive Disease Is a New Pattern of Progression in Cancer Patients Treated by Anti-PD-1/PD-L1," Cancer Therapy: Clinical, vol. 23, No. 8 (2017), pp. 1920-1928.

(Continued)

*Primary Examiner* — Gailene Gabel
(74) *Attorney, Agent, or Firm* — Pabst Patent Group LLP

(57) ABSTRACT

The present invention relates to the field of tumor immunology. It provides a method for identifying mutation-related human CD8+ T cells, in particular, tumor-specific T cells of a human subject, comprising analyzing CD8+ T cells of the subject by analysing the expression of at least one marker selected from a first group consisting of CD82, CD194, CD244, CD28, CD62L and CD55, and preferably, a marker selected from a second group comprising CD11a or CD18 or CD43. A preferred marker for mutation-related CD8+ T cells is CD82, which may be analysed in combination, e.g., with CD11a. Without the need to identify any epitope to which T cells reacts, this method can advantageously be used to isolate the entire individual pool of mutation-related T cells, and, optionally, to identify the sequence of a mutation-related TCR, which allows for generation of transgenic T cells expressing the TCR. Compositions substantially comprising tumor-specific $CD82^{hi}CD8+$ T cells and/or $CD194^{hi}$, $CD244^-$, $CD28^+$, $CD62L^+$ and/or $CD55^+$ $CD82^{hi}CD8+$ T cells can be used for treatment of a cancer patient, e.g., by adoptive T cell transfer. The method of the invention can also be used for diagnostic purposes to identify human mutation-related T cells or diagnosing a tumor disease or for testing responses of a cancer patient to an immune stimulatory therapy, preferably, a therapy with a checkpoint inhibitor.

16 Claims, 15 Drawing Sheets

(56)                    References Cited

OTHER PUBLICATIONS

Woller, Norman, et al., "Virus-induced tumor inflammation facilitates effective DC cancer immunotherapy in a Treg-dependent manner in mice," The Journal of Clinical Investigation, vol. 121, No. 7 (2011), pp. 2570-2582.

Khalaf, Natalia, et al., "Natural History of Untreated Hepatocellular Carcinoma in a US Cohort and the Role of Cancer Surveillance," Clinical Gastroenterology and Hepatology, vol. 15 (2017), pp. 273-281.

Chen, Zhan-Hong, et al., "Comparison of five staging systems in predicting the survival rate of patients with hepatocellular carcinoma undergoing trans-arterial chemoembolization therapy," Oncology Letters, vol. 15 (2018), pp. 855-862.

Carrasco, Javier, et al., "CD45RA on human CD8 T cells is sensitive to the time elapsed since the last antigenic stimulation," Blood, vol. 108, No. 9 (2006), pp. 2897-2905.

Lebel-Binay, S., et al., "CD82, member of the tetra-span-transmembrane protein family, is a costimulatory protein for T cell activation," J. Immunology, vol. 155 (1995), pp. 101-110.

Garcia-Carijo, Andrea, et al., "Determinants for Neoantigen Identification," Frontiers in Immunology, vol. 10 (2019).

Gros, Alena, et al. "Prospective identification of neoantigen-specific lymphocytes in the peripheral blood of melanoma patients," with supplementary text and figures, Nature Medicine, vol. 22, No. 4 (2016).

Summons to Attend Oral Proceedings, Issued by EP Patent Office, EP Application No. 20789997.2, issued Feb. 10, 2025.

International Search Report, PCT/EP2020/079038, mailed Mar. 22, 2021 (19 pages).

Solinas, Cinzia, et al., "The immune infiltrate in prostate, bladder and testicular tumors: An old friend for new challenges," Cancer Treatment Reviews, vol. 53 (2017), pp. 138-145.

Ott, Patrick A., et al., "An Update on Adoptive T-Cell Therapy and Neoantigen Vaccines," ASCO Educational Book (2019) (10 pages).

* cited by examiner

B     Spnb2-R913L

DC-induced T cells ratio T cell numbers to d7 (%)

- ● M1
- ■ M2
- ▲ M3
- ▼ M4 time (d)

tumor-induced T cells ratio of T cell numbers to d7 (%)

- ● M1
- ■ M2
- ▲ M3
- ▼ M4 time (d)

marker pentamer

| 2nd line pembrolizumab | 2x pembrolizumab | 4x pembrolizumab |

B

C

| analyte | 04/30/2015 | 05/07/2015 | 06/12/2015 |
|---|---|---|---|
| CRP (<6 mg/l) | 229.9 | 186.3 | 3.4 |
| LDH (<250 U/l) | 440 | 458 | 184 |

D blood sample for PBMC isolation (July 2015)

Screen of cellular expression patterns on PBMCs healthy controls (control arm)

CD82

CD11a

B regressing cancer patient

Generally between 1-3% positive CD8 T cells in healthy donors

A

B                                    cancer patients (no CPI)

CD82

CD11a

A 13 3 months
22.7% remission 37 4 months
23.5% remission 38 5.5 months
20.9% stable 39 pre-treatment
10.7%

39 6 weeks
22.7%

40 pre-treatment
2.8%

40 2 weeks
8.1%

41 pre-treatment
35%

41 9 weeks
51.6%

42 pre-treatment
10%

42 6 weeks
20.1%

CD82

CD11a

B 22 (smoker)

donor 1: strong sunburn
donor 2: sunburn
donor 3: UV-treatment
(30 x 311 nm),
no sunburn 44 pre-treatment      44 2 weeks      44 4 weeks              44 6 weeks 16.7%                 5.6%            5%

CD82

CD11a

A                     B               C naive gate          pathogen-spec. gate      tumor-spec. gate

7%                  9.9%                     84.8%

CD194 (CCR4)

CD11a

A                     B               C naive gate          pathogen-spec. gate      tumor-spec. gate

Q4 99,9%            Q4 26,5%                 Q4 98,1%

CD18

CD11a

Fig. 15 A-D
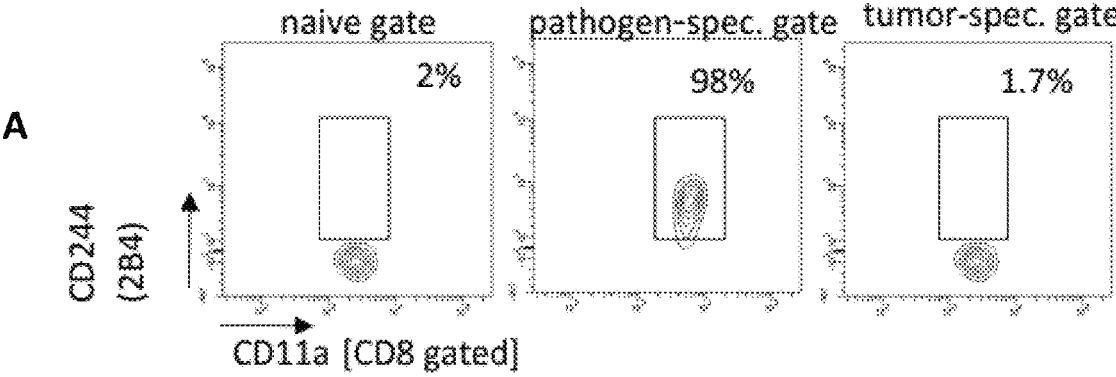
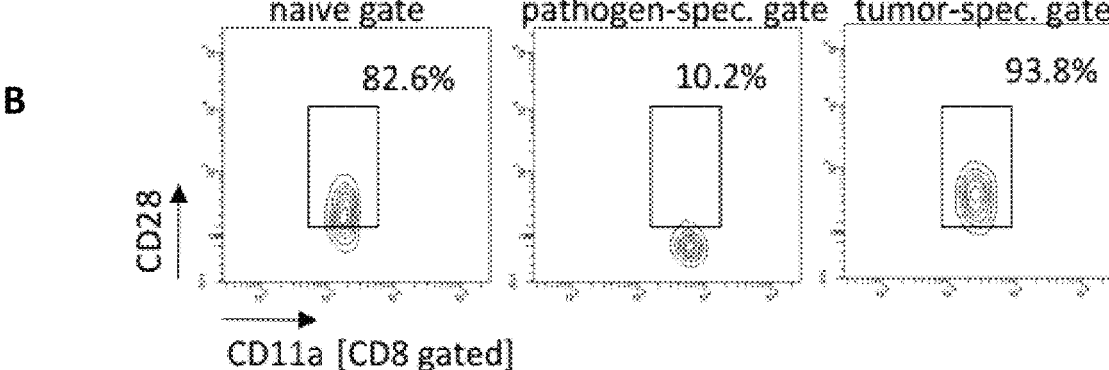
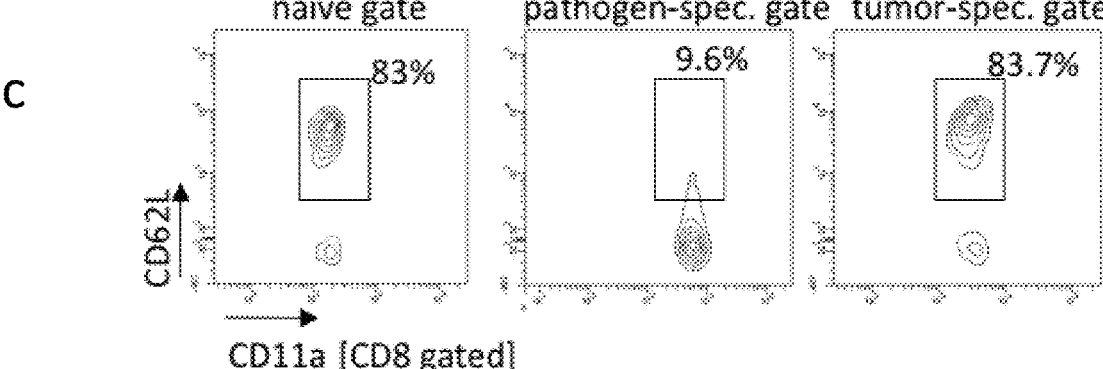
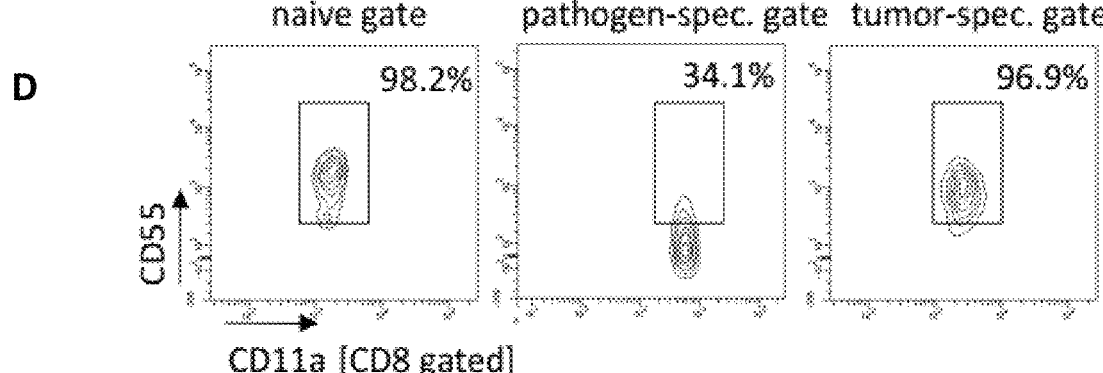

TCR-INDEPENDENT MOLECULAR IDENTIFICATION OF MUTATION-RELATED AND TUMOR-SPECIFIC T CELLS

The present invention relates to the field of tumor immunology. It provides a method for identifying mutation-related human CD8+ T cells, in particular, tumor-specific T cells of a human subject, comprising analyzing CD8+ T cells of the subject by analysing the expression of at least one marker selected from a first group consisting of CD82, CD194, CD244, CD28, CD62L and CD55, and preferably, a marker selected from a second group comprising CD11a or CD18 or CD43. A preferred marker for mutation-related CD8+ T cells is CD82, which may be analysed in combination, e.g., with CD11a. Without the need to identify any epitope to which T cells reacts, this method can advantageously be used to isolate the entire individual pool of mutation-related T cells, and, optionally, to identify the sequence of a mutation-related TCR, which allows for generation of transgenic T cells expressing the TCR. Compositions substantially comprising tumor-specific $CD82^{hi}CD8+$ T cells and/or $CD194^{hi}$, $CD244^-$, $D28^+$, $CD62L^+$ and/or $CD55^+$ $CD82^{hi}$ CD8+ T cells can be used for treatment of a cancer patient, e.g., by adoptive T cell transfer. The method of the invention can also be used for diagnostic purposes to identify human mutation-related T cells or diagnosing a tumor disease or for testing responses of a cancer patient to an immune stimulatory therapy, preferably, a therapy with a checkpoint inhibitor.

The immune system has evolved several mechanisms to protect the host against cancer. Each of them has to be undermined or evaded during cancer development to enable tumor outgrowth. Tumor outgrowth is mainly controlled by CD4+ and CD8+ T cells. During tumor development, cancer immunoediting occurs. There are three phases, elimination, equilibrium and escape [Ostroumov et al. Cell. Mol. Life Sci. 2018; 75:689-713; Dunn et al., Annu Rev Immunol 2004; 22:329-360]: After cellular transformation, in the elimination phase, nascent tumor lesions trigger an immune response that specifically eliminates these lesions, thus protecting the host from cancer. When, however, the immune response is incapable of completely clearing the tumor cells, but still prevents tumor outgrowth, an equilibrium phase occurs. The process of incomplete elimination promotes the generation of tumor cell variants with decreased immunogenicity. Following this selection process, sculpted or immunoedited tumor cells with low immunogenicity expand to a clinically manifest tumor. Yet, there is evidence that the immune system does not shape tumor immunogenicity towards complete tolerance. For example, when tumor-infiltrating T cells were isolated from tumor tissue, expanded in vitro and then retransferred into lymphopenic patients, this had impressive clinical effects [Dudley et al. Science 2002; 298:850-854].

Apart from T cell-induced selection of tumor cells towards those with reduced immunogenicity, another important mechanism affecting tumor-suppressive T cell responses is the induction of a dysfunctional state, anergy, or even apoptosis of these cells. It has been shown that low immunogenicity is not necessarily an inherent feature of T cell epitopes from immunoedited tumors [Knocke et al. Cell Reports 2016; 17: 2234-2246].

Some cancers are protected from immune attack by stimulating immune checkpoint targets, key regulators of the immune system that, when stimulated, can dampen the immune response to an immunologic stimulus. For example, PD-1 is the transmembrane programmed cell death 1 protein (also called PDCD1 and CD279), which interacts with PD-L1 (PD-1 ligand 1, or CD274). PD-L1 on the cancer cell surface binds to PD1 on an immune cell surface, which inhibits immune cell activity. It appears that upregulation of PD-L1 on the cell surface of cancer cells may inhibit T cell-mediated clearance. Antibodies that bind to either PD-1 or PD-L1 or other negative immune stimulatory ligands upregulated by the tumor cells or their ligands and that block the interaction may thus block inhibitory checkpoints and restore function of the cancer immune cycle. Clinically approved checkpoint inhibitors (or immune checkpoint inhibitors) target the molecules CTLA4, PD-1, and PD-L1.

However, the overall response rate (ORR) to checkpoint inhibitor therapy is low. Depending on the tumor entity, it rarely surpasses 20%. So far, there is no reliable prediction with biomarkers which patients respond to the therapy. In some tumor entities, an expression of PD-L1 correlates with a response. Often, a high mutational load, i.e., a high number of mutations in the tumor, correlates with a response to checkpoint inhibitor therapy. Ray et al. [J. Immunol. 2009; 183:7672-82] found that $CD11a^{hi}$ $CD8^{lo}$ expression (i.e, high expression of CD11a and low expression of CD8) on T cells in peripheral blood from mice characterizes antigen-experienced cells. In contrast, the authors show that naïve T cells display a $CD11a^{lo}$ $CD8^{hi}$ phenotype.

If the patient responds to immune checkpoint inhibitor therapy, the immune reaction is highly specific to the patients. There are some mutations in oncogenes and tumor suppressor genes that occur frequently (e.g., Ras or p53 mutations), but it is estimated that at least 95% of all mutations are specific for individual patients. This individuality renders the analysis of tumor immune responses difficult, and basically requires a complete sequencing or an algorithm-based prediction for neoepitopes followed by labor-intensive immune cell analysis [Castle et al. Cancer Res 2012; 72:1081-1091; van Rooij et al., J Clin Oncol 2013; 31:e439-e442]. Even if some T cell epitopes are found in these approaches, the identification of the entire tumor-specific T cell pool will be an unattainable task. Correctly identified epitopes to which the T cells are reactive can be isolated by peptide-MHC multimer technology. For acute myeloid leukemia, a method for isolating tumor-specific T cells through the identification of T cells capable of establishing stable interactions with leukemic cells has also recently been reported [Garcia-Guerrero et al. Front. Immunol. 2018; 9:1971-1986]. However, it appears difficult to transfer that method to isolation of T cells from non-hematological malignancies. Huang et al. [Nature 2017; 545:60-65] could show that after immune therapy, T cells were KI-67 positive, and this proliferation marker thus correlated with a therapeutic response.

The current main analytic means for cancer patients under immune therapy are imaging methods allowing for a comparison of the tumor size under the therapy. If possible, tumor markers are also used for evaluation. Other predictive or analytic biomarkers than those mentioned are presently under investigation. The analysis if the patient responds to therapy with checkpoint inhibitors is typically carried out between week 8 and 12 of therapy. If the tumor clearly progresses, the therapy with checkpoint inhibitors is halted, and another therapeutic approach is usually chosen.

One important issue for immune checkpoint inhibitor therapy is the occurrence of side effects. Depending on the medicaments used, the probability for occurrence of auto-immunity is significant (in about 10-35% of patients), and there can be various forms thereof, some life-threatening. This leads to a need for close monitoring, as this side effect can be controlled, e.g., by corticosteroids and stop of the therapy. It thus appears beneficial to know as early as possible in the therapy if the patient has any benefit, i.e., if the patient responds to the therapy.

In light of this, the invention solves the problem of providing an easy method for analysis and/or isolation of mutation-related, e.g., tumor-specific human CD8+ T cells that does not require knowledge of the specific antigen of the T cells or use of imaging methods.

The invention provides a method for identifying mutation-related CD8+ T cells of a human subject, comprising analysing the expression of at least one marker selected from a first group consisting of CD82, CD194, CD244, CD28, CD62L and CD55 of CD8+ T cells of the subject, wherein CD82$^{hi}$ cells and/or CD194$^{hi}$ cells and/or CD244$^-$ cells and/or CD28$^+$ cells and/or CD62L$^+$ cells and/or CD55$^+$ cells are identified as mutation-related CD8+ T cells. The markers of the first group are preferably all present, or can be present independently of each other.

In a preferred embodiment, the method comprises identifying mutation-related CD8+ T cells of a human subject, comprising analysing the expression of CD82 of CD8+ T cells of the subject, wherein CD82$^{hi}$ cells are identified as mutation-related CD8+ T cells. The method is based on the surprising finding that a high expression level of CD82 is a marker for mutation-related CD8+ T cells.

CD82 is broadly expressed by a variety of cells including monocytes, granulocytes, lymphocytes, epithelial cells, endothelial cells, and fibroblasts. CD82 has so far mainly been characterized as a tumor suppressor gene, or rather, a metastasis suppressor gene. It is a cell surface protein from the group of tetraspannins and is also designated Tspan-27. It has previously been identified as a costimulatory protein for T cell activation [Lebel-Binay et al. J Immunol. 1995; 155:101-110]. Expression of this gene has been shown to be downregulated in tumor progression of human cancers and can be activated by p53 through a consensus binding sequence in the promoter. CD82 suppresses metastasis by multiple mechanisms, including inhibition of cell motility and invasion, promotion of cell polarity as well as induction of senescence and apoptosis in response to extracellular stimuli. A common feature of these diverse effects is CD82 regulation of membrane organization as well as protein trafficking and interactions, which affects cellular signaling and intercellular communication [Tsai et al. FEBS Lett. 2011; 585(20):3166-3173].

In the context of the invention, it was found that, while CD82 is present on all CD8 T cells, the expression levels vary greatly, and cells with varying expression levels represent different subtypes: CD82$^{lo}$ expression levels correlate to T$_{EMRA/CM}$ (effector memory cells re-expressing CD45RA/central memory), CD82$^{int}$ (i.e., intermediate expression of CD82) to T$_{EM/CM}$ (effector memory/central memory) and CD82$^{hi}$ to mutation-related T cells. In particular, as shown herein, cancer patients have significantly higher numbers of CD82$^{hi}$CD8+ T cells than healthy subjects. This also applies to smokers, wherein the number of CD82$^{hi}$CD8+ T cells correlates with the number of smoking pack years, and for subjects having an acute sunburn. Other subjects with a high exposure to mutagens (such as UV radiation for sunburn, mutagens in tobacco smoke, other mutagenic radiation or exposure to other mutagens) are also expected to have significantly higher numbers of CD82$^{hi}$CD8+ T cells than healthy subjects without genotoxic exposure.

Thus, a mutation-related CD8+ T cell is a T cell associated with exposure of a subject to mutagens, which may or may not yet have led to development of a clinically apparent cancer or tumor disease. Accordingly, mutation-related T cells may, e.g., be specific for a tumor antigen, such as a neoantigen, a cancer-testis antigen, or a differentiation antigen. It is assumed that neoantigens play the dominant role [Gubin et al. Nature 2014; 515(7528):577-581].

In the context of the invention, the mutation-related T cells may be selected from the group comprising tumor-specific T cells, smoking-related T cells or sunburn-related T cells. Preferably, they are tumor-specific T-cells.

The inventor further found that human CD194$^{hi}$ CD8+ T cells are also mutation-related T cells. CD194 is also designated CCR4, i.e., C—C chemokine receptor 4. The protein belongs to the G protein-coupled receptor family. It is a receptor for the CC chemokines CCL2 (MCP-1), CCL4 (MIP-1), CCL5 (RANTES), CCL17 (TARC)[8], and CCL22 (Macrophage-derived chemokine) (wikipedia). CCR4 is often expressed on leukemic cells in cutaneous T-cell lymphoma (CTCL), and consequently, an antibody to the target is investigated for CTCL [https://www.healio.com/news/hematology-oncology/20171128/fda-grants-priority-review-to-mogamulizumab-for-cutaneous-tcell-lymphoma: FDA grants priority review to mogamulizumab for cutaneous T-cell lymphoma November 2017].

The inventor further found that human CD244– CD8+ T cells are also mutation-related T cells. CD244 is also designated Natural Killer Cell Receptor 2B4. It is a cell surface receptor expressed on natural killer cells (NK cells) and some T cells, mediating non-major histocompatibility complex (MHC) restricted killing. This marker is an activation marker absent from naive cells.

The inventor further found that human CD28+ CD8+ T cells can also be mutation-related T cells. CD28 is the receptor for CD80 and CD86, and one of the proteins expressed on T cells that provide co-stimulatory signals required for T cell activation and survival. It is particularly important for activation of naïve cells. After activation, CD28 is often downregulated. Surprisingly, expression on mutation-related cells has been found to be high.

The inventor further found that human CD62L+ CD8+ T cells can also be mutation-related T cells. CD62L is also designated L-selectin. It is an cell adhesion molecule that plays an important role in homing, e.g., for homig of naïve cells to peripheral lymph nodes.

The inventor further found that human CD55+ CD8+ T cells can also be mutation-related T cells. CD55 is also designated complement decay-accelerating factor or DAF. It interferes with activation of the compement cascade.

Interestingly, some of these markers show a similarity of mutation-related CD8+ T cells to naive cells. However, the secretion of cytokines and the memory phenotype show that thee cells are not naive. In particular, if these markers are used for isolation of mutation-related T cells, these cells are further distinguished from naïve cells, e.g., by analysis of CD45RA/RO. Mutation-related T-cells are CD45RA$^-$ and CD45RO$^+$. Further, naïve cells express CCR7, which is also expressed by the mutation-related cells.

The invention shows that the phenotype of T cells associated with exposure of a subject to mutagens, e.g., tumor-specific T cells, differs from the phenotype of T cells associated with the exposure of a subject to pathogens, e.g., viral or bacterial pathogens, or with the induction of T cell immunity by dendritic cell (DC)-based vaccination. Without intending to be bound by the theory, it may be the microenvironment in which the T cell activation takes place and/or the c-GAS/STING pathway of T cell activation itself that determines the CD82 expression levels of the CD8+T cells, or the expression levels of the other markers of the first group. Thus, mutation-related T cells are essentially non pathogen-specific T cells. They may be elicited to clear altered cells of the own organism, and targets may include tumor antigens, transplantation antigens or mutation-related alterations due to exposure to mutagens such as radiation or genotoxic mutagens. Possibly, T-cells directed to autoimmunity-related antigens in CD8+ mediated autoimmunity such as Type I diabetes, may also be mutation-related T cells, as such autoantigens may erroneously trigger a CD8 T cell response in a similar microenvironment.

For the present invention, 371 cell surface antigens were used to screen peripheral blood mononuclear cells (PBMC) of a patient strongly responding to an immune checkpoint inhibitor, pembrolizumab, in comparison to a healthy donor. CD4, CD8 and CD11a were also stained in a multi-color FACS (fluorescence-activated cell sorting) analysis. CD82 was found to be a highly specific and reproducible marker for mutation-related CD8+T cells. The method of the invention thus preferably comprises analysing the expression of CD82 of CD8+ T cells of the subject, wherein CD82$^{hi}$ cells are identified as mutation-related CD8+ T cells.

In a further screen, CD194 was also found to be a highly specific and reproducible marker for mutation-related CD8+T cells. As shown in the figures below, of the naïve CD8+ cells, about 7% were shown to be CD194+. Of the pathogen-specific cells, 9.9% were shown to be CD194+. of the tumor-specific CD8+ cells, 84.8% were shown to be CD194+.In another embodiment, the method of the invention comprises analysing the expression of CD194 of CD8+ T cells of the subject, wherein CD194$^{hi}$ cells are identified as mutation-related CD8+ T cells.

Further markers were also found to be markers for mutation-related CD8+ T cells:

As shown in the figures below, of the naïve CD8+ cells, about 2% were shown to be CD244$^-$. Of the pathogen-specific cells, 98% were shown to be CD244$^-$. Of the tumor-specific CD8+ cells, 1.7% were shown to be CD244$^-$. In another embodiment, the method of the invention thus comprises analysing the expression of CD244 of CD8+ T cells of the subject, wherein CD244$^-$ cells are identified as mutation-related CD8+ T cells.

Of the naïve CD8+ cells, about 82.6% were shown to be CD28$^+$. Of the pathogen-specific cells, 10.2% were shown to be CD28$^+$. of the tumor-specific CD8+ cells, 93.8% were shown to be CD28$^+$. In another embodiment, the method of the invention thus comprises analysing the expression of CD28 of CD8+ T cells of the subject, wherein CD28$^+$ cells are identified as mutation-related CD8+ T cells.

Of the naïve CD8+ cells, about 83% were shown to be CD62L$^+$. Of the pathogen-specific cells, 9.6% were shown to be CD62L$^+$. Of the tumor-specific CD8+ cells, 83.7% were shown to be CD62L$^+$. In another embodiment, the method of the invention thus comprises analysing the expression of CD62L of CD8+ T cells of the subject, wherein CD62L$^+$ cells are identified as mutation-related CD8+ T cells.

Of the naïve CD8+ cells, about 98.2% were shown to be CD55$^+$. Of the pathogen-specific cells, 34.1% were shown to be CD55+. Of the tumor-specific CD8+ cells, 96.9% were shown to be CD55+. In another embodiment, the method of the invention thus comprises analysing the expression of CD55 of CD8+ T cells of the subject, wherein CD55$^+$ cells are identified as mutation-related CD8+ T cells.

Optionally, the mutation-related or tunor-specific T cells qualify as mutation-related according to at least 2, at least 3, at least 4, at least 5 or, preferably, all 6 markers of the first group of markers.

The inventors found that the mutation-related and tumor-specific CD8+T cells also expressed a specific pattern of CD11a. It should be noted that, in the human system, the expression of CD11a on the cells identifies as mutation related cells by expression of at least one marker from the first group, e.g., CD82$^{hi}$ T cells, was intermediate (i.e., higher than the expression of CD11a on CD11a-CD8+ naïve T cells and lower than the maximal expression of CD11a on CD8+ pathogen-specific T cells. As shown in the figures, the CD82$^{hi}$CD11a$^{int}$ cells formed a distinct population of CD8+ T cells, which can be, e.g., visualized by FACS analysis.

Therefore, the method of the invention preferably further comprises analysing the T cells for the expression levels of CD11a, wherein CD11a+ cells are identified as mutation-related cells, preferably, if the subject is a human, CD11a$^{int}$ cells.

The inventors further found that CD18, which is known to be non-covalently associated with CD11a, also has nearly identical expression patterns on mutation-related T cells. Thus, instead or in addition to CD11a expression, CD18 expression can be analysed, wherein CD18$^{int}$ cells are identified as mutation-related cells.

Consequently, the method of the invention may also comprise analysing the expression of CD18 of the CD8+ T cells, wherein CD18$^{int}$ cells that are further identified as mutation-related by a marker from the first group as defined above, e.g., CD82$^+$, are identified as mutation-related cells.

Further, the inventors found that CD43, which is also designated leukosialin, also has a similar expression patterns on mutation-related T cells. Thus, instead or in addition to CD11a or CD18 expression, CD43 expression can be analysed, wherein CD43$^{int}$ cells are identified as mutation-related cells. Consequently, the method of the invention, in one embodiment, comprises analysing the expression of CD43 of the CD8+ T cells, wherein cells positive for at least one of the first marker group, e.g., CD82$^{hi}$ that are further CD43$^{int}$ cells are identified as mutation-related cells.

It is noted that there are significant differences with regard to surface markers of mutation-related T cells for the murine and the human system. In the context of the invention as claimed herein, the subject thus is a human subject, most preferably, a human patient, such as a patient having a tumor disease.

If the subject is a mouse, the mutation-related cells are CD11a$^{high}$ (CD11a$^{hi}$) rather than CD11a$^{int}$. In the case of mice, it has also been found that mutation-related CD8+ T cells are CD8$^{hi}$. For mice, the T cells may thus be analyzed for the extent of CD8 and/or CD11a expression, wherein CD8$^{hi}$ and/or CD11a$^{hi}$ cells are identified as mutation-related (preferably, tumor-specific) T cells. Preferably, said cells are CD8$^{hi}$ and CD11a$^{hi}$.

The method disclosed herein may be adapted to a non-human system, e.g., in a mouse, rat, rabbit, guinea pig, pig, monkey or ape, to test the mutagenic potential of agents. An agent can be considered a mutagenic agent if the frequency of mutation-related T cells detected according to the method of the invention increases upon exposure to the agent (e.g., within 1 week or within 2 weeks).

If the subject has not been exposed to potent mutagens, as the examples herein show, there is a strong correlation with the presence of a tumor of undefined size. Accordingly, the mutation-related T cells may then be identified as tumor-specific T cells. Of course, the mutation-related T cells may also be identified as tumor-specific T cells by other means, e.g., proliferation or expression of activation markers in response to tumor antigens, e.g., in the context of contact with tumor cells or tumor-specific peptides or MHC multimers, by confirmation that the subject has a tumor by other diagnostic means, infiltration of the T cells in a tumor, or by identification of the epitope to which the T cell reacts as a tumor antigen. Thus, e.g., $CD82^{hi}$ T cells of a smoker who has a tumor are also considered tumor-specific T cells.

It is noted that the population identified, e.g., of $CD82^{hi}CD8+$ T cells or $CD194^{hi}CD8+$ T cells does not necessarily completely consist of mutation-related or tumor-specific T cells due to staining issues, poor resolution of the measurement, or other technical restrictions, but the majority of T cells in this population is considered to be mutation-related or tumor-specific.

In a further analysis, in the majority of 70 healthy donors, it was found that most donors had a proportion of 1-3% $CD82^{hi}$ cells of all CD8+ T cells, which is therefore considered normal. Only 13% of these subjects had a higher frequency of $CD82^{hi}CD8+$ T cells. If this group was differentiated into smokers and non-smokers, smokers had a significantly higher incidence of a raised proportion/frequency of $CD82^{hi}CD8+$ T cells (1/57 non-smokers versus 10/13 smokers). The number of pack years of smokers somewhat correlates with the level of $CD82^{hi}CD8+$ T cells. It should be noted that all subjects with 30 spy or more were positive for increased levels of mutation-related T cells (i.e., more than 3% $CD82^{hi}$ cells of all CD8+ T cells).

In contrast, in the tumor patients (who had not yet received an immunotherapy), there was a significant increase in the frequency of the $CD82^{hi}CD8+$ T cells (82% tumor patients (n=22) versus the control arm with 15% (n=70)). The numbers of $CD82^{hi}CD8+$ T cells were also increased after Dermatitis solaris, i.e., sunburn. Two subjects from the control group, for which the $CD82^{hi}CD8+$ T cell-frequency had already previously been determined before the sunburn, had increased frequencies of $CD82^{hi}CD8+$ T cells about 14 days after the sunburn. In the following weeks, these values decreased nearly to the basic value, supposedly due to an elimination of the mutated cells, which, in this context, can be assumed to be single mutated cells only, and a following contraction of the mutation-related T cell pool. In contrast, the frequency of $CD82^{hi}CD8+$ cells stayed high in smokers, e.g., for over 3 years in a smoker with 50 pack years.

The phenotype of $CD82^{hi}$ mutation-related T cells has been further analyzed in the context of the invention. One characteristic that has been found is that these cells have a memory phenotype different from the pool of pathogen-specific T cells. Mutation-related T cells, e.g., $CD82^{hi}CD8+$ T cells, do not express CD45RA. They can further be partly CCR7 positive. They can thus be considered a mixed population of central memory cells ($T_{CM}$) and effector memory cells ($T_{EM}$) that, in contrast to pathogen-specific cells, does not differentiate into $T_{EMRA}$ cells. Thus, in one embodiment of the method of the invention, the method further comprises analyzing the T cells for the presence of CD45RA, wherein CD45RA– cells are identified as mutation-related cells.

Upon activation, mutation-related T cells, e.g., $CD82^{hi}$ mutation-related T cells, may further secrete a different cytokine profile than pathogen-specific cells. Upon activation with PMA/ionomycin, pathogen-specific cells secrete both IFN-gamma and TNF-alpha. Tumor-specific cells rather do not secrete these cytokines (TNF-alpha-neg/IFNgamma-neg), or are single positive for TNF-alpha, while only low amounts are double positive for TNF-alpha/IFN-gamma.

It is also important to note that presence of a tumor does not necessarily mean that the patient has a high proportion (e.g., more than 3%) of mutation-related T cells, in particular, $CD82^{hi}CD8+$ T cells. Some patients may have lower proportion of such cells, which may however expand, e.g., in response to a checkpoint inhibitor therapy. However, most tumor patients (82% in this study) have more than 3%, often, more than 5% or 5-65% $CD82^{hi}CD8+$ T cells (i.e., $CD82^{hi}$ cells in the population of CD8+ T cells of a subject).

CD8+ T cells of the subject may be analyzed in a sample obtained from the subject, e.g., a blood sample, or in PBMC (peripheral blood mononuclear cells) isolated from the subject, e.g., isolated from blood through a Ficoll gradient, or in a tumor sample, e.g., a biopsy, or a resected tumor, or T cells isolated from said tumor sample, preferably, in a sample derived from blood. It is one of the advantages of the invention that the analysis does not require prior isolation or even identification of a tumor, and can be carried out based on a blood sample.

It is possible to separate T cells, and/or CD8+ T cells from other cells, e.g., by methods known in the art, before determining the expression of CD82 and/or other surface markers such as CD194. However, the analysis may also be carried out in one step.

Preferably, the method of the invention comprises contacting cells, e.g., blood cells or PBMC, with antibodies to CD82, i.e., antibodies capable of specifically binding to CD82, or antibodies to other surface markers as defined herein, such as CD194. The antibodies are preferably labelled. Alternatively, cells labelled with the antibodies, e.g., anti-CD82 antibodies, can be identified and/or isolated with a secondary antibody capable of specifically binding to said antibody, e.g., the anti-CD82 antibody. The secondary antibody may then be labelled. The antibodies may be monoclonal or polyclonal antibodies. Preferably, the antibodies are anti-human CD82 antibodies for detection of CD82 on human cells. Suitable antibodies to CD82 can be commercially available antibodies (e.g., from Biolegend (San Diego, CA); Miltenyi Biotech (Bergisch Gladbach, Germany)), or they can be generated by methods known to the skilled person. Preferably, the antibodies are directed to the human marker, e.g., anti-human CD194 antibodies are used for detection of CD194 on human cells. Suitable antibodies, e.g., to CD194, can be commercially available antibodies (e.g., from Biolegend (San Diego, CA); Miltenyi Biotech (Bergisch Gladbach, Germany)), or they can be generated by methods known to the skilled person.

Antibodies may be labelled with a detectable marker, e.g., with biotin, streptavidin, a His-tag or a fluorescent label, preferably, with a fluorescent label. Suitable labels are well known in the art, e.g., FITC, PE, Cy3, Cy5, APC, or quantum dots. If the antibodies are not labelled, they may still be selected, e.g., by binding to protein A or protein G.

The method of the invention may comprises flow cytometry, e.g., Fluorescence Activated Cell Sorting (FACS). Magnetic activated cell sorting (MACS) may also be used. Flow cytometric methods are advantageous, because it is easy to analyze for the presence of multiple markers with different fluorescent labels at the same time. For example, CD82 and/or another marker of the first group, preferably, CD82, CD8a or b, TCRα/β, and CD11a or CD18 or CD43, preferably, CD11a, may be analyzed at the same time. Preferably, CD8b is analysed at the same time, because that is advantageous in that it excludes MAIT cells. For analysis of TCRα/β it is advantageous to exclude CD8+γδ T-cells.

Preferably, for the flow cytometric analysis, CD8+ T cells, most preferably, CD8b+ TCRα/β T cells are gated and then analyzed for CD82 and/or expression of another marker of the first group, and CD11a and/or CD18 and/or CD43 expression, preferably, for CD82 and CD11a expression. In this visualization, the mutation-related, e.g., CD82$^{hi}$CD11$^{int}$ human, CD8+ T cell population can be easily distinguished from other populations, and, if desired, it can be isolated using a cell sorter or other means.

The antibodies may also be labelled with a magnetic bead. In particular, magnetic cell sorting for isolation of mutation-specific, e.g., tumor-specific T cells can easily be carried out in the clinic. Negative sorting, e.g., with magnetic cell sorting is also possible, e.g., depleting cells positive for CD4, CD14, CD16, CD19, CD20, CD36, CD45RA, CD56, CD123, CD235ab, TCR γ/δ, and/or TCR Vδ2 (e.g., with a MojoSort™ Human CD8 Memory T-cell Isolation Kit, Biolegend), wherein the cells are further depleted for CD244 cells, because preferred mutation-related cells are CD244$^-$. Negative sorting has the advantage that the isolated cells are untouched.

It is noted that the skilled person is routinely capable of differentiating between cells having a different expression level of a surface marker, e.g., by flow cytometric means. For example, CD8+ T cells negative for a specific marker show a staining comparable to the same cells only contacted with a control antibody, e.g., an isotype control. Different levels of surface expression correspond to different binding levels of an antibody to the surface antigen, which may be directly or indirectly detected. CD8+ T cells having a high expression of a marker (e.g., CD82$^{hi}$) have a higher expression of said marker than such cells having an intermediate expression of said marker (if existent), or than such cells having a low expression of said marker (e.g., CD82$^{lo}$). As described herein and shown, e.g., in FIG. 3E, CD8+ T cells having CD82$^{hi}$ phenotype can advantageously be detected as a separate population of cells by co-staining with CD11a, whereas the CD82$^{hi}$ cells are CD11a$^{in}$, i.e., the expression of CD11a is lower than that of the CD8+ T cells having the highest expression of CD11a (CD11a$^{hi}$) and higher than the expression of the CD8+ T cells having the lowest expression of CD11a (CD11a$^{lo}$).

In one embodiment, the invention thus provides a method for providing a mutation-related human CD8+ T cell, comprising carrying out the method of the invention, as described herein, and isolating a mutation-related T cell. Preferably, the mutation-related T cell is a tumor-specific T cell. Of course, a population of mutation-related CD8+ T cells can also be isolated in this way.

If a single mutation-related T cell is isolated, it may be cultivated e.g., under conditions leading to proliferation of the T cells, for example, in the presence of IL-2 or other proliferative or homeostatic cytokines. Thus, mutation-related T cell or tumor-specific T cell clones may be generated.

On this basis, the invention also provides a method for providing a nucleic acid encoding a TCR of a mutation-related human CD8+ T cell. Upon generation of a mutation-related CD8+ T cell clone or single cell PCR with a focus on the recombined TCR genes, the sequence of the TCR of the mutation-related T-cell is identified or sequenced. Such a TCR can be recombinantly expressed, e.g., in another T cell, optionally, in another human T cell. The invention thus also provides a method for providing a mutation-related, in particular, a tumor-specific CD8+ T cell, comprising providing a nucleic acid encoding the TCR of a mutation-related, preferably, tumor-specific CD8+ T cell and expressing the TCR in a CD8+ T cell.

In a population of mutation-related T cells, the mutation-related T cell pool can be analysed, e.g., by using TCR-α- and TCR-β-specific antibodies identifying defined TCR-chains (e.g. Vα7.2, Vβ13) to identify the dominant T cell clone within the tumor-specific pool. Isolation and tumor-specific validation of this clone (e.g., by flow cytometric means or by MACS) may circumvent carryover of T cells possibly mediating autoimmune properties when used for adoptive T cell transfer. Sequencing of the TCRs is an alternative option.

The invention thus also provides a method for providing a mutation-related, in particular, a tumor-specific CD8+ T cell, comprising providing a dominant T cell clone validated to be tumor-specific, and a nucleic acid encoding the TCR of said mutation-related, preferably, tumor-specific CD8+ T cell and expressing the TCR in a CD8+ T cell.

For adoptive T cell therapy, for example, a TCR obtainable by a method of the invention can be expressed in an individualized approach or in an HLA-restricted manner. The T cell or T cells transformed to express the TCR may be derived from a patient having a tumor, wherein preferably, said TCR is capable of recognizing an antigen of said tumor on an MHC expressed by said patient. Thus, typically, the patient and the subject from which the TCR is derived will share at least one MHC. The subject from which the TCR is derived may also be the patient to be treated. In this case, the transformed T cell may be derived from the patient.

In one embodiment, the invention also provides a method for identifying a tumor epitope of a tumor capable of inducing tumor-specific T cells, comprising providing a mutation-related CD8+ T cell, as described herein, and identifying the epitope to which the T cell is reactive. In contrast to prior art method, the identification of the T cell epitope to which the T cell is reactive is, here, not a prerequisite for isolating the T cells, but the epitope can be identified in an easier manner, e.g., based on screening if the epitope leads to activation of the mutation-related T cells. The invention further provides a method for providing a composition comprising at least 90%, preferably, at least 95%, at least 99% or essentially only mutation-related T cells, comprising carrying out the method of the invention and isolating mutation-related T cells. Preferably, the mutation-related T cells are tumor-specific T cells. The isolation may, e.g., be carried out by flow cytometric methods, wherein, preferably, CD8+CD82$^{hi}$CD11$^{int}$ T cells are isolated. Alternatively, e.g., CD8+CD194$^{hi}$CD11a$^{int}$ T cells, CD8+CD82$^{hi}$CD11a$^{int}$ T cells or CD8+CD194$^{hi}$CD11a$^{int}$ T cells may be isolated. CD8+CD82$^{hi}$CD18+ T cells, CD8+ CD194$^{hi}$CD18$^{int}$ T cells or CD8+ CD82$^{hi}$CD194$^{hi}$CD11a$^{int}$CD18$^{int}$ T cells may be isolated. The method may further comprise cultivating and/or activating the mutation-related T cells, e.g., to generate higher amounts of said T cells. The T cells may also, optionally, be treated with checkpoint inhibitors in vitro. The method optionally further comprises formulating the mutation-related T cells as a pharmaceutical composition, which is preferred in the context of treatment of a patient.

In one embodiment, the invention also provides a composition comprising at least 90%, preferably, at least 95%, at least 99% or essentially only mutation related cells as defined herein, preferably, CD82+CD11a+CD8+ T cells. The composition may alternatively comprise at least 90%, preferably, at least 95%, at least 99% or essentially only CD8+CD194$^{hi}$CD11a$^{int}$ T cells, CD8+CD82$^{hi}$CD18$^{int}$ T cells, CD8+CD194$^{hi}$CD18$^{int}$ T cells, CD8+

11

CD82$^{hi}$CD11a$^{int}$CD18$^{int}$ T cells, CD8+ CD194$^{hii}$CD11a$^{int}$CD18$^{int}$ T cells or CD8+ CD82$^{hi}$CD194$^{hi}$CD11a$^{int}$ CD18$^{int}$ T cells. Said composition optionally is a pharmaceutical composition. A pharmaceutical composition is biologically acceptable and may comprise, e.g., at least one biologically acceptable pharmaceutical excipient and/or solvent.

A pharmaceutical composition of the invention comprising tumor-specific CD8+ T cells of the invention may be for use in treatment of a cancer patient. Adoptive T cell transfer has been found to be an effective means for treatment of cancer, both with regard to solid tumors and hematological malignancies. The invention thus also provides a pharmaceutical composition of the invention comprising tumor-specific CD8+ T cells for use in adoptive T cell transfer to a cancer patient.

Treatment protocols for treating cancer by adoptive T cell transfer are, e.g., known in the art. To avoid an immune response against the transferred T cells, and to ensure recognition of the tumor by the T cells, the mutation-related CD8+ T cells are preferably derived from the patient. Alternatively, allogeneic T cells may be used, typically from a subject having the same kind of cancer-specific mutations and and a matching HLA. This can be determined, e.g., by screening of the tumor-specific T-cells and a sample form the tumor of the patient. Genetically modified T cells isolated by the method of the invention may also be used, which may be, e.g., genetically modified to avoid an immune response against the T cells.

The invention also provides a method of treating a cancer patient, comprising administering to said patient tumor-specific CD8+ T cells isolated or provided by a method of the invention, e.g., derived from the blood of the patient, or transformed with a TCR derived from a tumor-specific CD8+ T cells isolated or provided by a method of the invention. Preferably, the tumor-specific CD8+ T cells are derived from the blood of the patient.

In the context of the invention, a cancer or tumor may be a solid tumor or a hematological malignancy. For example, it may be a lymphoma such as non-Hodgkin's lymphoma, Hodgkin's lymphoma, Merkel-cell carcinoma, leukemia, such as B cell acute lymphoblastic leukemia, melanoma, lung cancer, kidney cancer, bladder cancer, head and neck cancer, cholangiocellular carcinoma, squamous cell carcinoma, retinoblastoma, hepatocellular carcinoma (HCC), gastric cancer, prostate cancer, pancreatic cancer, colorectal carcinoma, cervical cancer, bile duct cancer, neuroblastoma, breast cancer, or (osteo-)sarcoma.

The invention also provides a method of diagnosing a tumor disease in a subject, comprising carrying out the method of the invention. If mutation-related T cells, preferably, at least CD82$^{hi}$CD8+ T cells, or alternatively, e.g., CD194$^{hi}$CD8+ T cells, are found in a sample from the subject in a proportion of more than 3%, preferably, more than 5%, more than 10% or more than 20%, there is an increased likelihood that the subject has mutated cells, in particular, cancer cells or a tumor. This likelihood is particularly high for non-smokers, but it also applies to smokers. Preferably, if the subject has an acute sunburn or has had an acute sunburn, he/she is excluded from analysis, or the analysis is repeated more than 1, more than 2, more than 4, more than 5, more than 8 or more than 10 weeks after the sunburn has healed, depending on the strength of the sunburn. The method of diagnosis optionally further comprises confirming the diagnosis of a cancer, e.g., by analysis of tumor markers and/or imaging methods, if a high proportion (more than 3%, preferably, more than 5%, more than 10% or more than 20%) of mutation-related T cells, preferably, at least CD82$^{hi}$CD8+ T cells, or alternatively, e.g., CD194$^{hi}$CD8+ T cells, are found in a sample from the subject. The method of diagnosis of the invention thus has the advantage of providing an easy and quick method for diagnosis, at least in a first step, which only requires analysis of a blood sample of the subject.

In another embodiment, the invention shows a correlation between an expansion of the proportion of the tumor-specific T cells, preferably, CD82$^{hi}$CD8+ T cells, or alternatively, e.g., CD194$^{hi}$CD8+ T cells, in a cancer patient treated with an immune stimulatory therapy, in particular, a therapy with a checkpoint inhibitor, with the response to said therapy. The invention thus also provides a method of testing the response of a cancer patient to an immune stimulatory therapy, preferably, a therapy with a checkpoint inhibitor, comprising carrying out the method of the invention. In this context, the cancer patient is the subject. It has surprisingly been found that an expansion of mutation-related (or tumor-specific) CD8+ T cells correlates with a response to the therapy. In this context, an increase of the proportion of mutation-related, e.g., CD82$^{hi}$CD8+ T cells, by at least 10%, at least 20%, at least 30%, at least 40%, preferably, at least 50%, at least 75% or even 100-300% is considered to be an expansion of said population. For examples, stable disease has been observed in a patient having an expansion of said population to about 10% CD82$^{hi}$CD8+ T cells, or remission has been obtained for a patient having an expansion of said population to about 20% CD82$^{hi}$CD8+ T cells. The level of expansion may correlate with the magnitude of the response that is present prior to therapy, but that is not required. The expansion is typically seen during a time range of about 2-9 weeks after the start of therapy, sometimes even later, e.g., up to 28 weeks after the start of the therapy, compared with the proportion of the CD82$^{hi}$CD8+ T cells before therapy or at the start of therapy (e.g., on the same day), if there is a response.

The invention also provides an analytic tool for conventional therapies, such as chemotherapy and/or radiation, and/or checkpoint inhibitors for use in treatment of cancer, wherein the presence of mutation-related (or tumor-specific), preferably, CD82$^{hi}$ CD8+ T cells, as described herein, at the beginning of the therapy and during the course of the therapy with the checkpoint inhibitor is monitored, using the method of the invention, and the therapy is continued if there is an expansion of the mutation-related, preferably, CD82$^{hi}$CD8+ T cells. Preferably, said therapy comprises checkpoint inhibitor therapy, optionally, in combination with another therapy such as chemotherapy and/or radiation.

This invention also allows for analysis of a follow-up care post treatment, when a complete response or remission is achieved. In almost any case it is unforeseeable whether remnant tumor cells still persist and will continue to grow out again to clinically manifest tumors afterwards. As shown in examples in the results, mutation-related T cells contract e.g., to a non-detectable level or a level typical for healthy subjects, i.e., less than 3% upon absence of the antigen, i.e. when the tumor is cleared. In this case, the invention allows for a sensitive indirect detection of residual tumors. If post treatment or close to post treatment, e.g., 2-24, optionally, 4-12 weeks after treatment, tumor-specific T cells are still present, this indicates that the tumor still persists in the patient. Obtaining this information, may help to decide about continuation or discontinuation of the treatment. Thus, in one embodiment, the invention provides a method of diagnosing a tumor disease in a cancer patient, comprising carrying out the method of the invention to identify tumor-specific T cells, wherein, optionally, the method is carried out to identify residual disease during or after treatment of a cancer patient that has caused remission. Checkpoint inhibitor therapy (CPI) may be therapy with an agent, e.g., an antibody or a small molecule (up to 900 Da), preferably, an antibody, that binds to either PD-1, PD-L1, CTLA-4 or other immunomodulatory ligands, wherein the checkpoint inhibitors are capable of restoring tumor immunity. Exemplary drugs are nivolumab, pembrolizumab, spartalizumab, atezolizumab, avelumab, durvalumab, ipilimumab, or tremelimumab. The checkpoint inhibitors may be used for treatment of the cancer diseases for which they are admitted to the marked, e.g., in the treatment regimen known in the art. For example, nivolumab is approved to treat melanoma, lung cancer, kidney cancer, bladder cancer, head and neck cancer, and Hodgkin's lymphoma. Pembrolizumab is approved to treat melanoma and lung cancer, and has been successfully used to treat hepatocellular carcinoma (HCC). Spartalizumab may be used for treatment of solid tumors and lymphomas. Checkpoint inhibitor therapy may be used for first line or second line therapy. Checkpoint inhibitors may be used alone or in combinations, e.g., with cancer vaccination, or in combination with other antibodies, e.g., a VEGF inhibitor such as axitinib.

Finally, the invention may be for use in treatment of hyperprogressive disease (HPD) in the context of immune checkpoint inhibition [Champiat et al., Clin Cancer Res 2016; 23(8); 1920-8]. HPD is an adverse effect of CPI, in which treated patients suddenly suffer a rapid onset of tumor growth. In the results of this invention, one case was observed were application of nivolumab led to a severe contraction of the tumor-specific T cell pool within weeks followed by an unexpected death of the patient after three infusions. To circumvent the complications derived from HPD, this invention can be used to isolate and expand tumor-specific T cells as described above prior to CPI, and in case of occurring HPD, the treatment is discontinued and these cells can be adoptively transferred to reconstitute tumor immunity. The invention thus also provides a composition comprising at least 90% of tumor-specific human T cells, e.g., CD82$^{hi}$CD11a$^{in}$CD8+ T cells, preferably, T cells isolated from the patient prior to treatment with a checkpoint inhibitor, for use in adoptive transfer to a patient having hyperproliferative disease, wherein the treatment with the checkpoint inhibitor is discontinued. This treatment may be particularly advantageous if it is determined that the pool of human tumor-specific T cells, e.g., human CD82$^{hi}$CD11a$^{in}$CD8+ T cells, contracts significantly upon treatment with the checkpoint inhibitor.

In the context of the invention, "about" is understood to mean+/–10%, if not otherwise mentioned. "A" is to be understood to mean "at least one", if not otherwise mentioned. Thus, for example, a therapy with a checkpoint inhibitor also includes a therapy with a combination of several checkpoint inhibitors.

All literature cited herein is herewith explicitly included by said reference. The following examples are intended to illustrate, but not to limit the invention.

BRIEF DESCRIPTION OF THE DRAWINGS

FIG. 1Aa shows vectors used in experiments and results already described in detail in Knocke et al. Cell Rep 2016; 17:2234-46. Ab depicts liver tumors expressing antigens included in said vectors in the absence of T cell tumor-immunogenicity, i.e., after injection of the the control vector 1 (1/top)) and in the presence of potent T cell tumor-immunogenicity elicited by vector 2 (2/bottom), respectively. Ac shows dot plots of tumor-specific CD8 T cells of OVA and Spnb2-R913L elicited by vector 2. In FIG. Ad H and E (Hematoxylin and eosin) stained liver sections reveal massive lymphocytic tumor infiltration in tumors with potent immunogenicity elicited by vector 2. FIG. 1B shows differences in CD8 expression levels between murine tumor-specific CD8+ T cells elicited by vaccination with DC and by cancer immunosurveillance.

Another HCC patient showed a positive cytokine response to CMV (cytomegalovirus) (FIG. 11B). CD8+ T cells were stimulated with a CMV-peptide and gated for IFN-γ and TNF-α (left blot) and then analyzed for CD11a and CD82 (right top blot). Upon gating, the virus-specific cells positive for both IFN-γ and TNF-α were restricted to CD8 CD11a$^{hi}$ CD82$^{lo}$ section.

Figure 12:
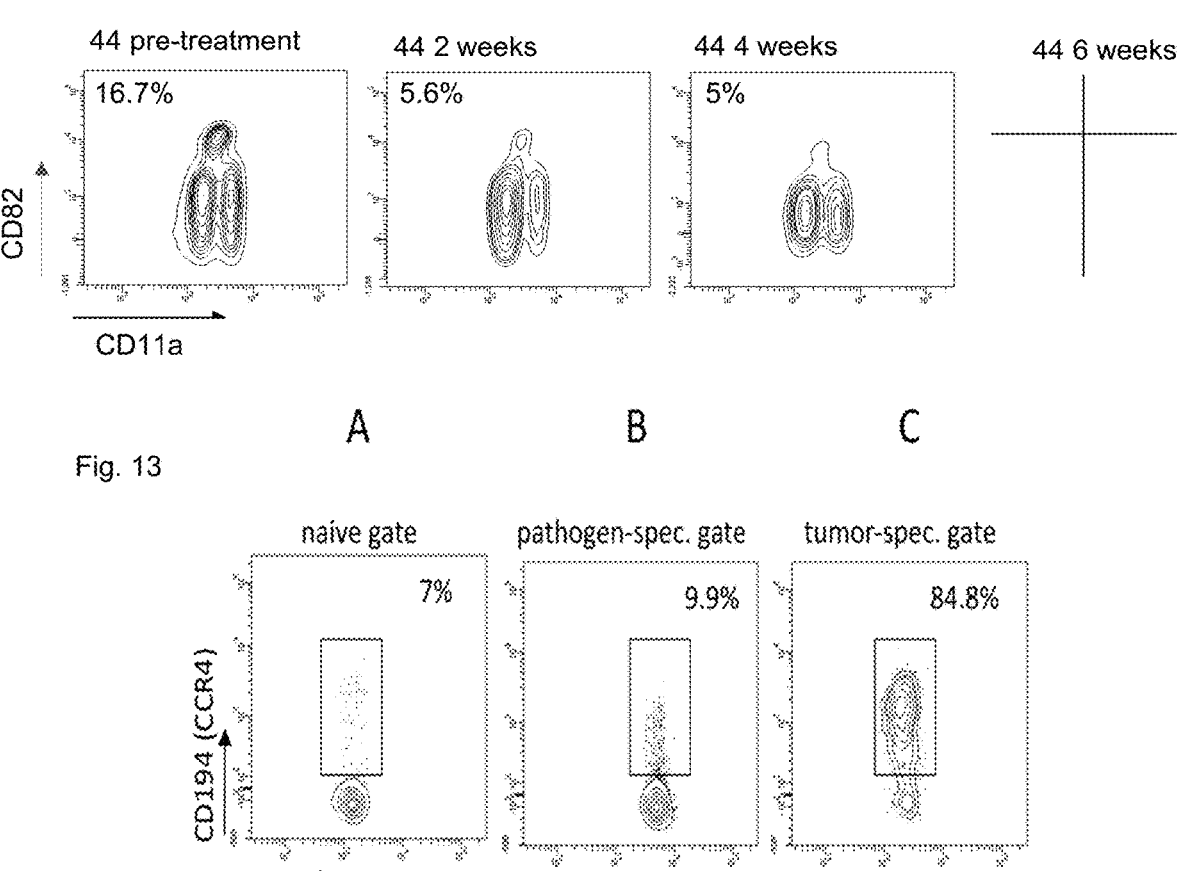

FIG. 12 shows contraction of the CD82$^{hi}$CD11a$^{int}$CD8+ T cells pool in a patient with hyperprogressive disease under CPI treatment.

Figure 13:

FIG. 13 shows that CD194 also is a marker for mutation-related, in particular, tumor-specific CD8+ cells. Of the CD8+ cells gated, in the naïve gate, there are 7% CD194+(or CD194$^{hi}$) cells (A), in the pathogen-specific gate, there are 9.9% CD194+ cells (B), and in the tumor-specific gate, there are 84.8% CD194+ cells (C).

Figure 14:
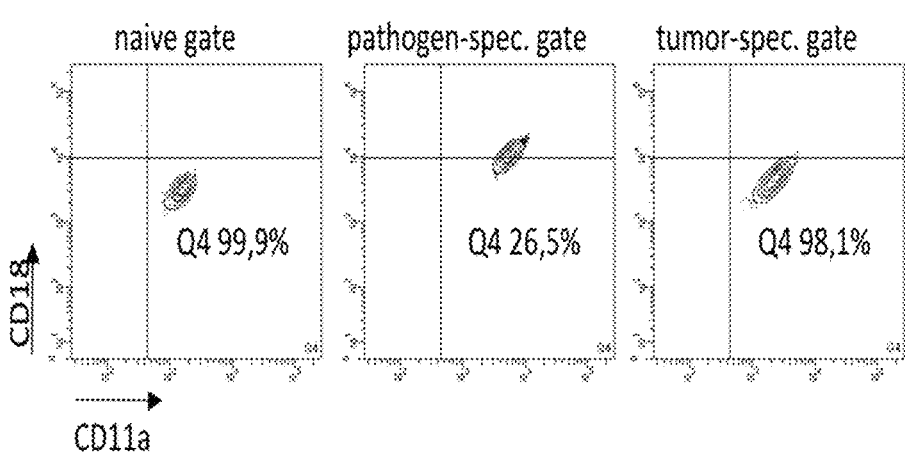

FIG. 14 shows that CD18 is coexpressed with CD11a, and can thus be used as an alternative marker. Of the CD8+ cells gated, in the naïve gate, there are 99.9% CD11$^{int}$ and CD18+ (i.e., CD18$^{int}$) cells (MFI CD18: 3215, MFI CD11a: 1630) (A), in the pathogen-specific gate, there are 26.5% CD11$^{int}$ and CD18+ (i.e., CD18$^{int}$) cells (MFI CD18: 22.256, MFI CD11a: 5956) (B), and in the tumor-specific gate, there are 98.1% CD11$^{int}$ and CD18+ (i.e., CD18$^{int}$) cells (MFI CD18: 4950, MFI CD11a: 2481) (C). The ratios are CD11a: N (naïve)/P (pathogen-specific): 0.288, CD18: N/P 0.272, CD11a T (tumor-specific)/P: 0.417, CD18 T/P: 0.444. It is noted that both CD11a and CD18 are expressed at an intermediate level on the tumor-specific CD8+ T cells, while in the pathogen-specific CD8+ T cells, expression of both markers is high.

Figure 15E:
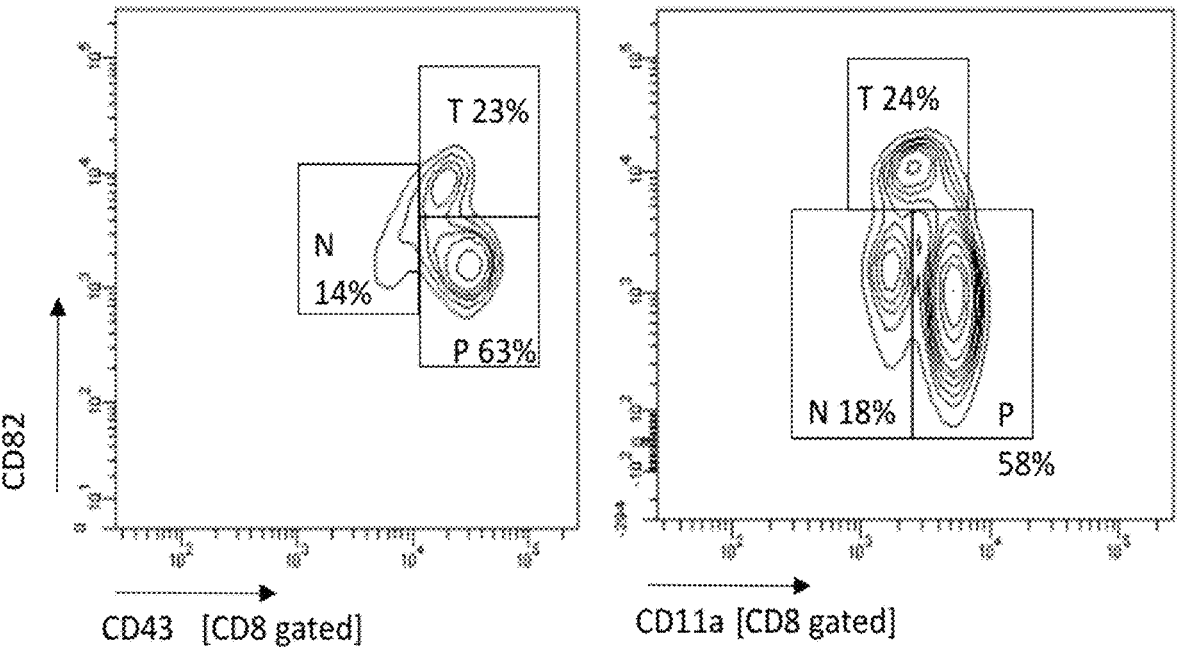

FIG. 15 shows expression of further markers for mutation-related, in particular, tumor-specific CD8+ cells. Expression is shown for each marker in naïve cells, pathogen-specific cells and tumor-specific cells. A: CD244, B: CD28, C: CD62L, D: CD55, E: CD43.

EXAMPLES

1. Animal Experiments

Figure 1:
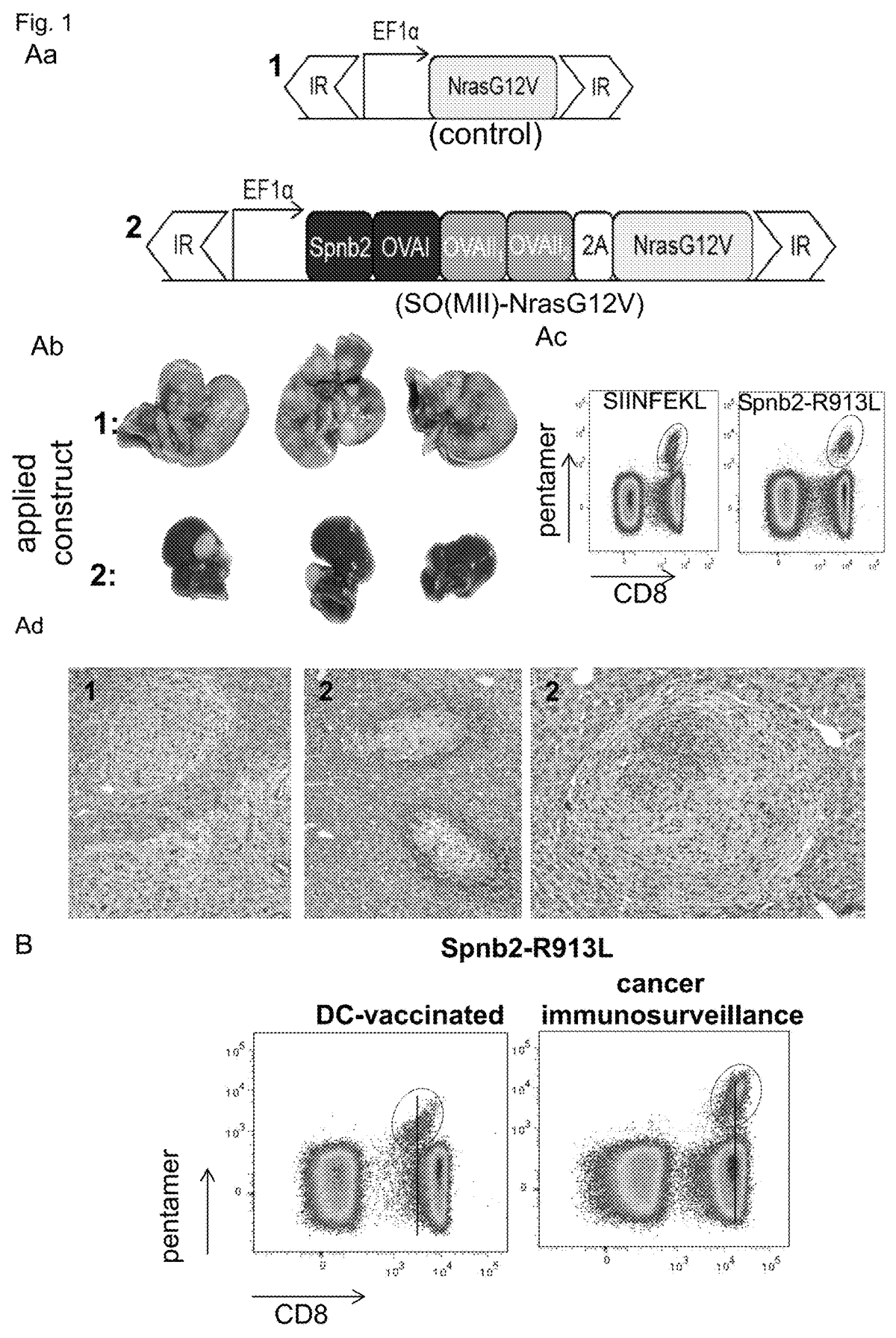

The mouse tumor model used for the analysis of T cell phenotypes has been described before [Knocke et al. Cell Rep 2016; 17:2234-46]. In brief, FIG. 1Aa shows transposon expression vectors to generate liver tumors that encoded epitope tags of highly immunogenic CD4 and CD8 T cell epitopes, such as Spnb2-R913L, SIINFEKL and both MHCclass II restricted OVA epitopes in combination with oncogenic Nras (including the G12V-mutation). Nras alone served as control. The tumor progression was severely inhibited in a T cell-dependent manner compared to the control group transfected with vector 1 (FIG. 1Ab). Tumor-specific T cells were detected with a pentamer (FIG. 1Ac). The HE histology shows signs of strong lymphocytic infiltration into the immunogenic tumors (FIG. 1Ac).

Figure 2:
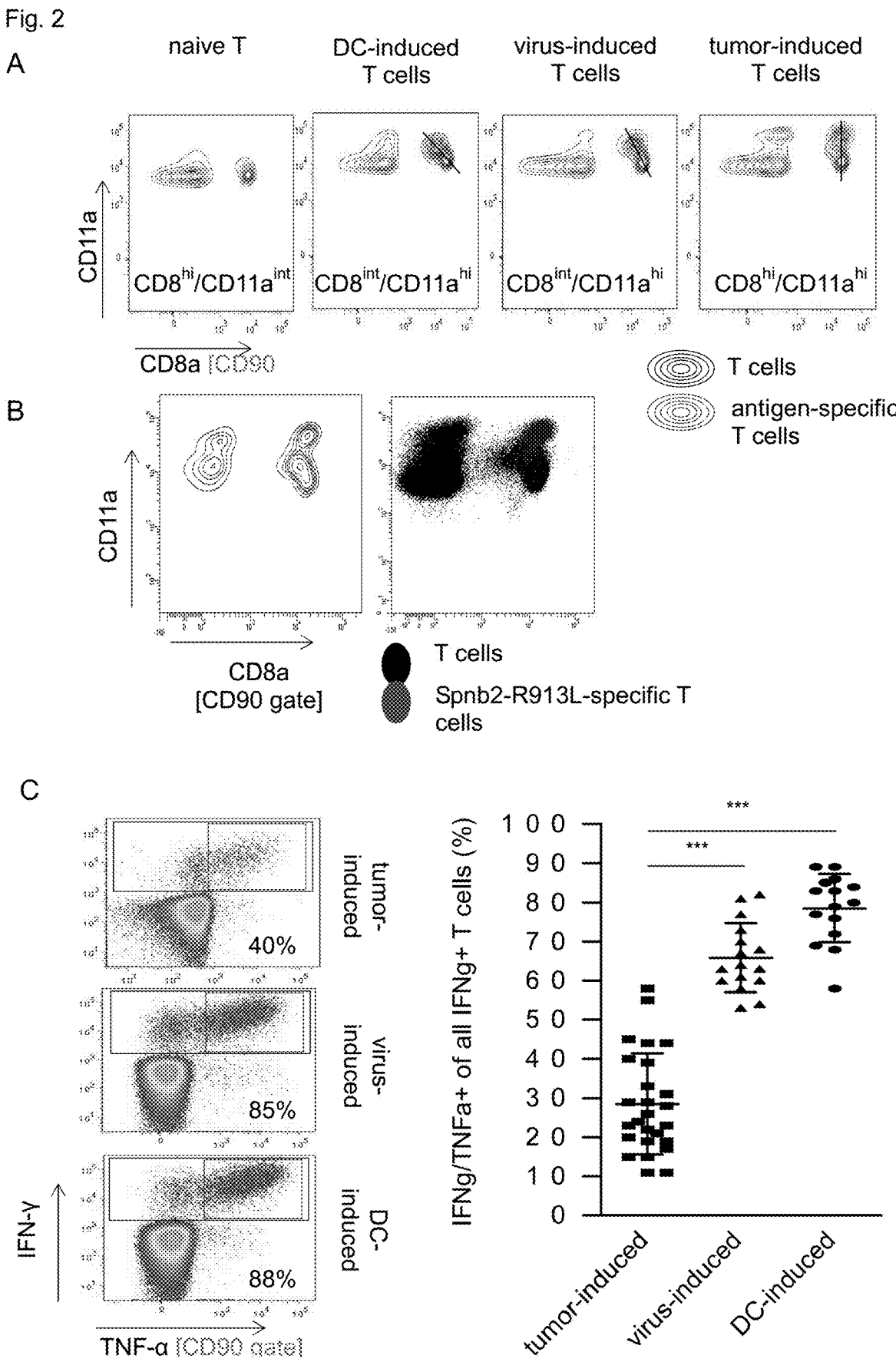
FIG. 2 shows differences in CD8 and CD11a expression levels on T cells derived from tumor-specific CD8+ T cells elicited by vaccination with DCs as described in Woller et al., J Clin Invest. 2011; 121(7):2570-2582, by virus-induced T cells, and by tumor-induced T cells. (A), CD8 and CD11a expression levels on T cells derived from a liver tumor in an overlay with tumor-specific T cells, which confirms the tumor specificity of the CD11a$^{hi}$ and CD8a$^{hi}$ T cells. (B), cytokine expression (C) and life cycle of these T cells (D).

To further analyze tumor-specific T cell responses in this model with an emphasis of the T cell phenotype, a T cell response against Spnb2-R913L elicited by a DC vaccine (described in [Woller et al., J Clin Invest. 2011; 121(7): 2570-2582]) was compared with a T cell response against the same specificity, but derived from a naturally elicited response in the mouse tumor model as described above (FIG. 2A). The results of flow cytometry using a Spnb2-R913L-specific pentamer show a decrease in CD8 expression in tumor-specific T cells when triggered by DC vaccination and unaltered expression levels of CD8 on these cells in mice with Spnb2-R913L-expressing tumors. Downregulation of CD8 in antigen-experienced T cells has been described by Ray et al. [J. Immunol. 2009; 183:7672-82]. The authors of this study used CD11a additionally to identify CD8$^{low}$ CD11a$^{hi}$ T cells as antigen-experienced cells. The present data, as shown in FIG. 2A, demonstrate that this phenotype complies with the phenotype of T cells derived from DC vaccination and virus-specific T cells. However, CD8+ T cells derived from immunogenic tumors display a different phenotype with CD8$^{hi}$ CD11a$^{hi}$ expression. Here, CD11a expression is reproducibly higher than CD11a expression on T cells derived from DC vaccination/viral infections. FIG. 2B shows a density plot in which CD8$^{hi}$ CD11a$^{hi}$ tumor-derived T cells are distinguishable from CD8$^{lo}$ CD11a$^{hi}$ pathogen-derived T cells, demonstrating that both populations do coexist and are not attributable to staining artifacts of flow cytometry (left plot). The plot on the right side proves that Spnb2-R913L-specific cells only occur in the CD8$^{hi}$ CD11a$^{hi}$ area (FIG. 2B).

Analysis of cytokine secretion of the respective T cells confirms the difference in the phenotype of T cells dependent on the kind of antigenic stimulation. Tumor-induced T-cells stain double positive for Interferon gamma and tumor-necrosis factor alpha at a significantly lower rate compared to virus-specific and DC-induced T cells. Each dot represents an individual mouse in the right graph of FIG. 2C.

Figures 2D, 2E:
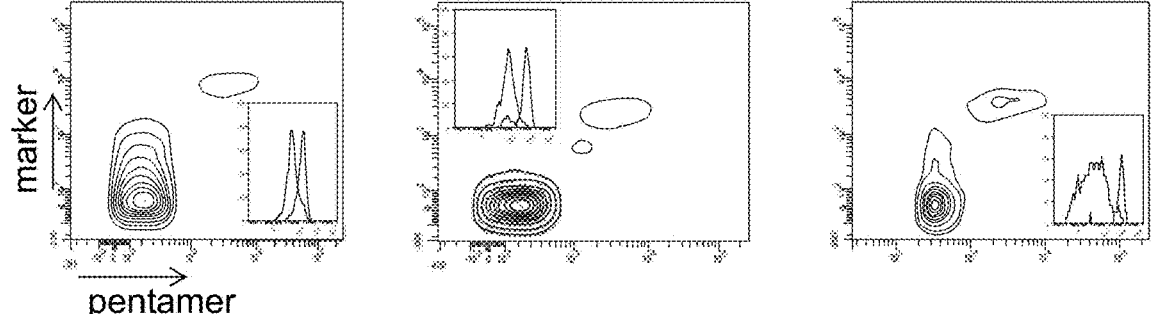
FIG. 2E confirms that the marker shown is also specific for pentamer-stained tumor-specific T cells. Thus, murine tumor-specific T cells have a unique phenotype.

Observing the kinetic of DC-induced T cells in a time course of 42 days showed that DC-induced T cells peak on day seven and contract rapidly until day 14. In contrast, the kinetics of tumor-induced T cells differ markedly. They appear to expand more slowly, but at a higher magnitude, and apparently more than one expansion is a naturally occurring phenomenon (FIG. 2D).

Thus, the data allows for the conclusion that tumor-induced T cells have a different phenotype than DC-induced T cells or pathogen-induced T cells.

To test if there are specific markers on CD8+ tumor-specific T cells to differentiate the phenotype of these cells from other CD8 T cells, a biomarker screen was performed. To this end, an antibody-based screen with flow cytometry of surface markers was performed. The source of screening material consisted of peripheral blood cells from mice that were injected with transposon plasmids as described above and that survived about 55 days. Those mice developed CD8$^{hi}$ CD11a$^{hi}$ T cells and CD8$^{lo}$CD11a$^{hi}$ T cells that were additionally stained with one of 243 PE-labelled murine screening antibodies (Legend Screen Kit (Biolegend)). The T cell population gated to CD8$^{lo}$ CD11a$^{hi}$ T cells, i.e., pathogen-specific CD8+ T cells, is depicted as a histogram of the corresponding screening marker with a grey line in the inlays. $CD8^{hi}$ $CD11a^{hi}$ T cells, i.e., tumor-specific T cells, are shown in the histogram with a black line. The histograms in FIG. 2E shows that the tumor-specific T cells stained by the pentamer are also positive for a marker not expressed by the pathogen-specific CD8+ T cells. Therefore, CD8 T cells from tumor-bearing mice were stained with a Spnb2-R913L-specific pentamer and the corresponding biomarker. As shown in FIG. 2D, cancer-specific CD8 T cells are sufficiently identified by a single staining with the biomarker alone, as double staining with the pentamer identifies tumor-specificity in each case. Thus, it is possible to identify tumor-specific T cells by reference to their phenotype based on surface protein expression in a TCR-agnostic manner.

2. Human Experiments—Marker Identification

Figure 3A:
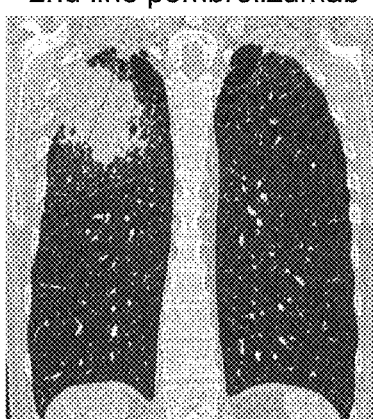
FIG. 3 documents the experiment described in more detail below for marker-identification of tumor-specific human CD8+ T cells (A-D).
FIG. 3E shows identification of a population of CD82$^{hi}$CD11a$^{in}$CD8+ T cells (bottom blots) specifically present in a regressing cancer patient, but not in a healthy donor, in comparison to the isotype control (for CD82 staining, top plots). The CD82$^{lo}$, CD82$^{in}$ and CD82$^{hi}$ populations can be easily distinguished.
Figure 3A:
Figure 3A:
Figure 3A:
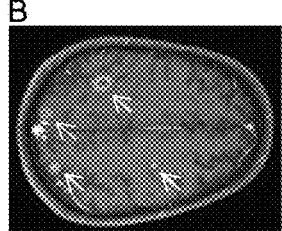
Figure 3A:
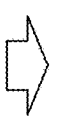
Figure 3A:
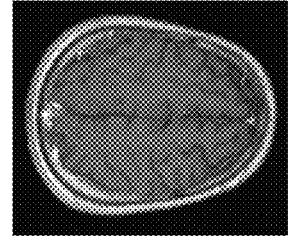
Figure 3A:
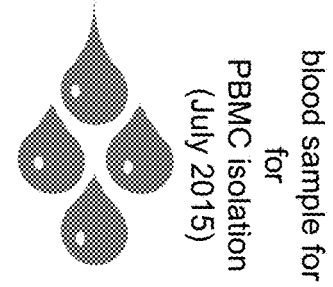
Figure 3A:
Figure 3A:
Figure 3E:
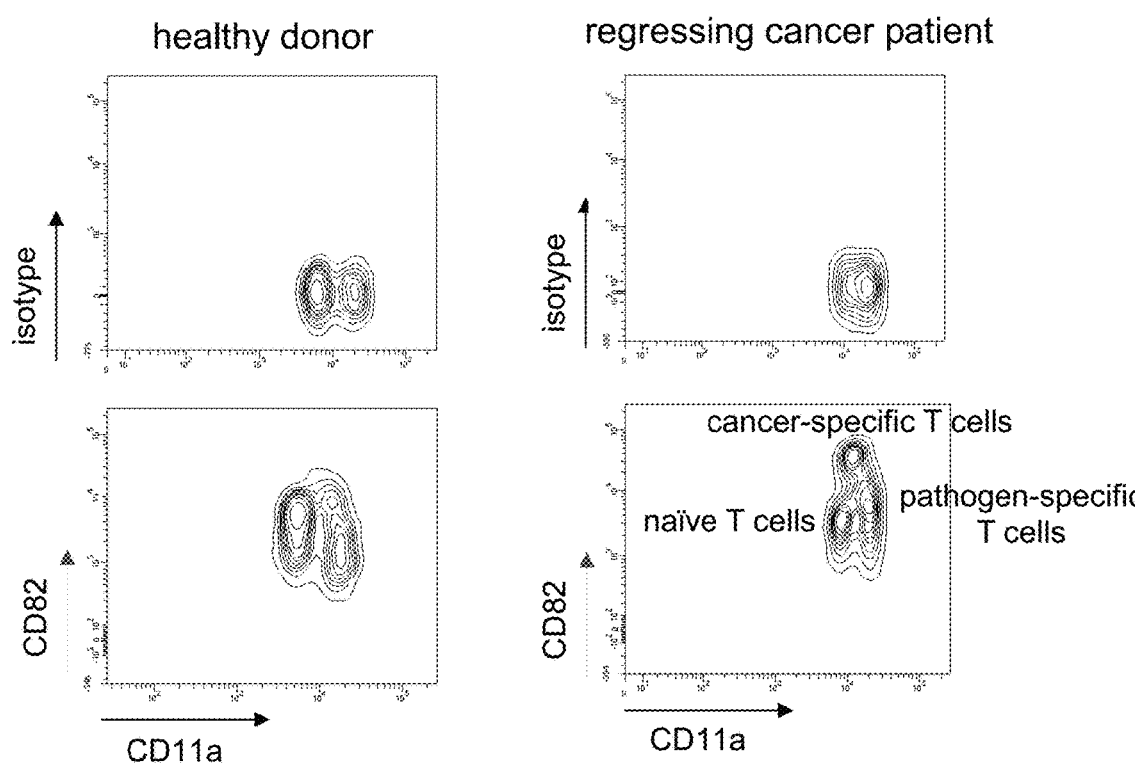

After obtaining clear evidence for a specific phenotype of cancer-induced CD8+T cells from a tumor mouse model, a similar screen was performed in human samples. A 40 years old male patient with a NSCLC (non-small cell lung cancer) stage IV suffering a progress after first line chemotherapy was treated with the PD-1 checkpoint inhibitor pembrolizumab. As shown in FIG. 3A, the primary tumor regressed markedly after four infusions of pembrolizumab. Additionally, bone-, liver-, and brain metastasis underwent a complete remission and tumor markers, such as CRP and LDH, normalized (FIG. 3B). At this time point, blood samples were obtained from the patient und compared with a healthy donor (FIG. 3C). The screening was done with 371 PE-labelled anti-human antibodies from the Legend Screen Kit (Biolegend) according to the manufacturer's recommendations (FIG. 3D). The following antibody panel from the same company was used: CD8a FITC (clone HIT8a), CD4 PerCP-Cy5.5 (clone OKT4), and CD11a APC (clone TS2/4). The screening revealed CD82 as one promising candidate among all screened surface markers. In FIG. 3E, the density plots of gated CD8+ T cells show CD11a on the X-axis and CD82 on the Y-axis. For CD82, a plot of an isotype is shown as well. The plot of the regressing cancer patient has an additional population with high expression of CD82 and intermediate expression of CD11a which is absent in the healthy control. Interestingly, in this population CD11a, with an intermediate expression level, also differs from the $CD11a^{hi}$ and $CD11a^{lo}$ population. Further characterization of $CD11a^{lo}$ T cells identified these cells as naïve T cells. Moreover, $CD11a^{hi}$ cells are antigen-experienced T cells (FIG. 10) and there is strong evidence that they are pathogen-specific as shown below. The CD8+ $CD11a^{int}$ $CD82^{hi}$ T cells are further characterized in the following experiments.

3. Analysis of Healthy Subjects and Cancer Patients

Figure 4A:
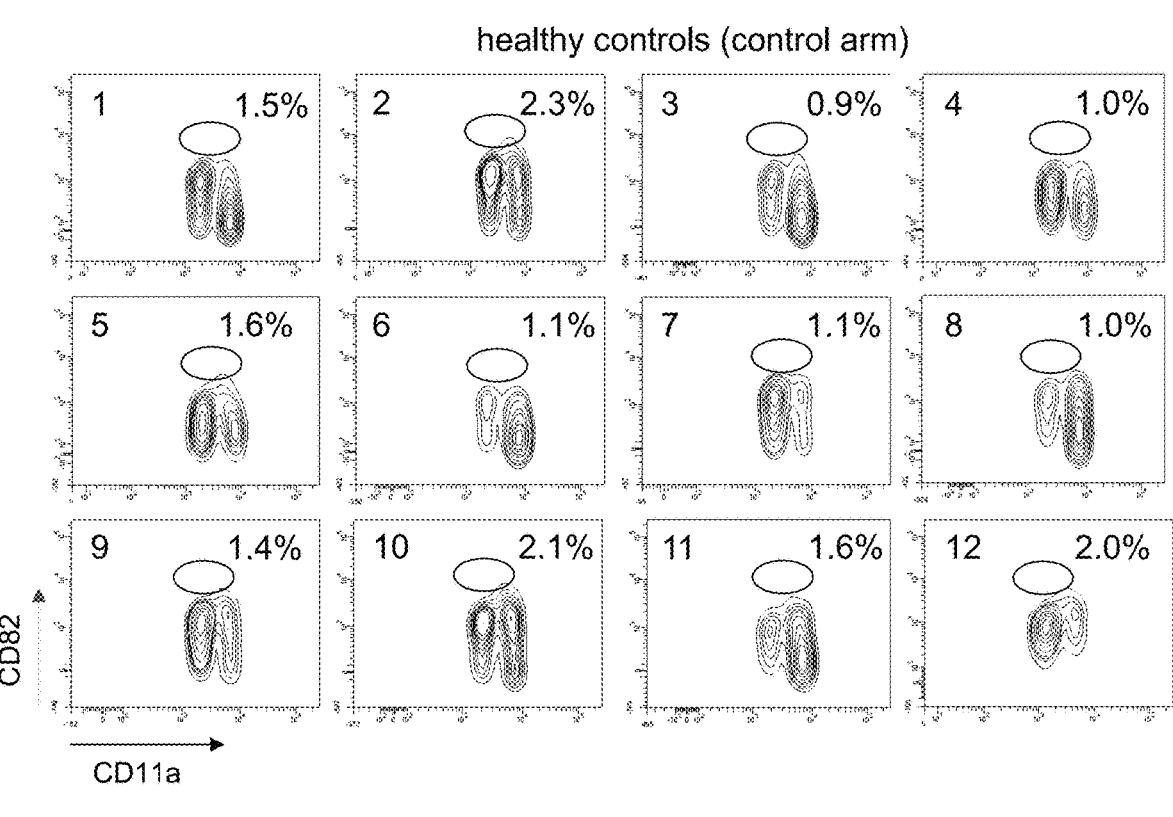
FIG. 4 shows the presence and frequency of CD82$^{hi}$CD11a$^{in}$CD8+ T cells in healthy control subjects (A, B) and in the regressing cancer patient (B). There are generally between 1-3% CD82$^{hi}$ positive CD8+ T cells in healthy donors.
Figure 4A:
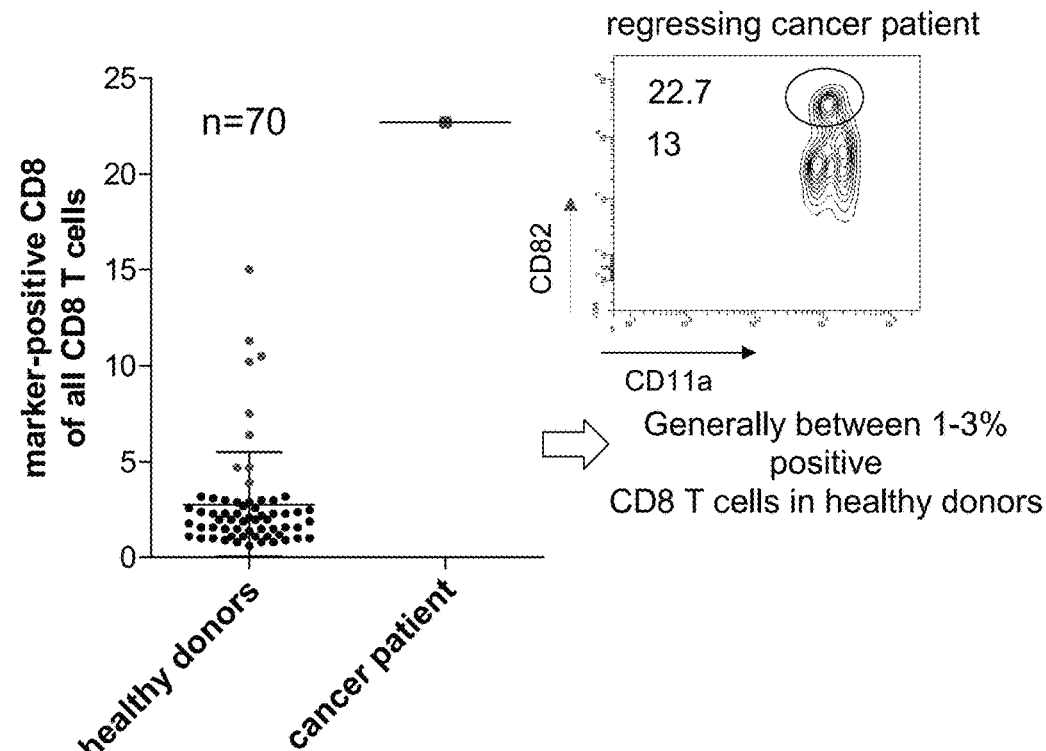

In the next step, a cohort of 70 healthy individuals volunteered in this study and donated blood to allow for characterization of expression patterns of CD8+ $CD11a^{int}$ $CD82^{hi}$ T cells. In FIG. 4A, representative density plots of these individuals are shown. In all figures, the plots are numbered in a consecutive manner for reference. Most healthy donors (59/70) had a CD8+ $CD11a^{int}$ $CD82^{hi}$ T cell population that accounted for three percent or less of the total CD8+ T cell pool. This is referenced as the normal value in healthy individuals. FIG. 4B shows the data compared to a regressing cancer patient for the purpose of comparison. Since 11 healthy donors had higher values, in part considerably higher, a subgroup analysis was performed.

Figure 5:
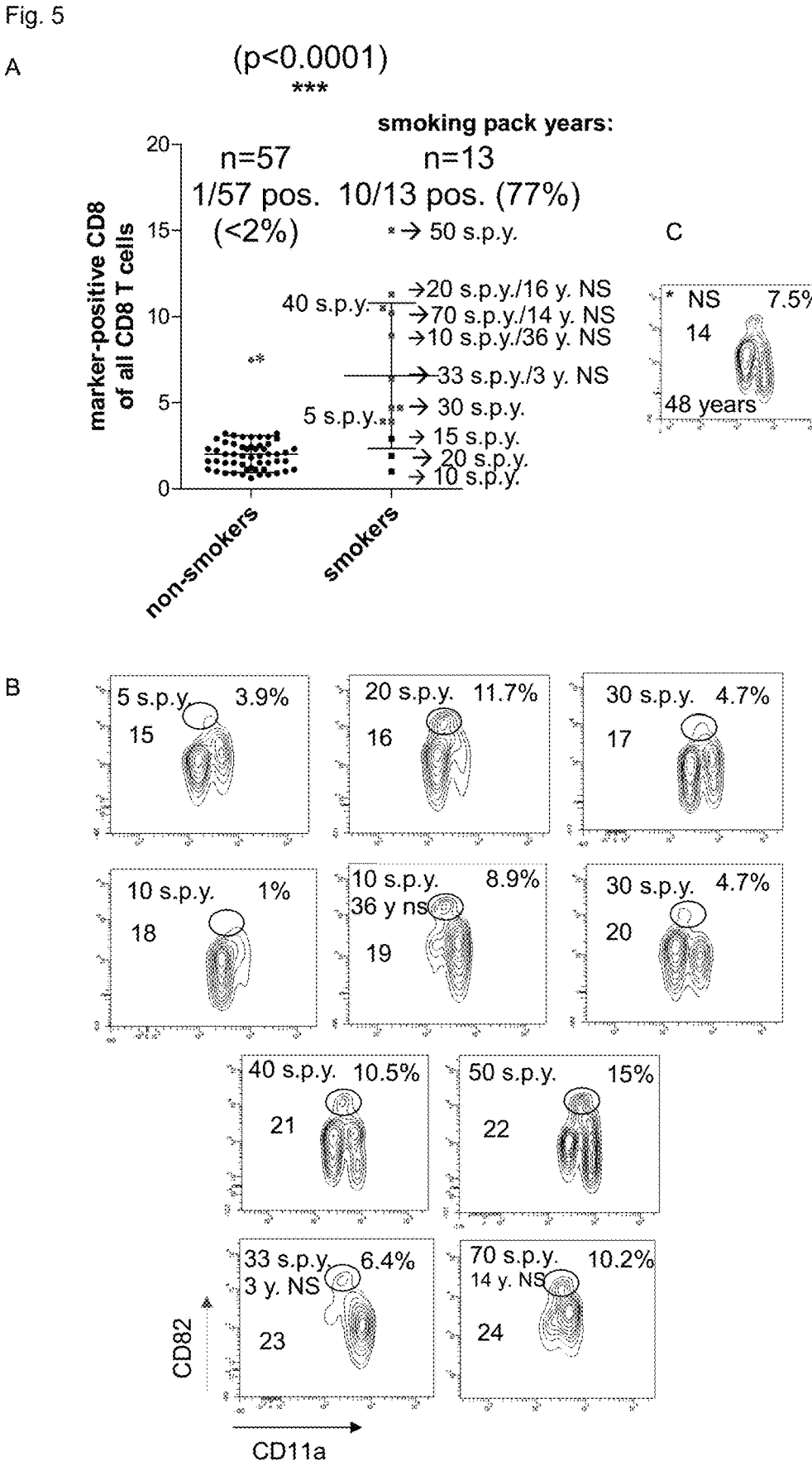
FIG. 5 shows the frequency and presence of CD82$^{hi}$CD11a$^{in}$CD8+ T cells in smokers and non-smokers (A, B). C shows the exceptional presence of an untypically high frequency of CD82$^{hi}$CD11a$^{in}$CD8+ T cells in a non-smoker not diagnosed to have a tumor.

In the subgroup analysis of healthy donors, non-smokers and smokers were separately investigated. There was a wide spread of individual smoking habits with regard of frequency and duration. Consequently, the smoking pack years (s.p.y.) were applied for each individual value as an indicator for the biological smoking burden (one s.p.y. equals one package of cigarettes per day for one year). Presenting the results in this way revealed a significant (p<0.0001) difference within these groups. 77% of smokers had elevated levels of CD8+ $CD11a^{int}$ $CD82^{hi}$ T cells, whereas <2% of the non-smoking arm was positive (NS=non-smoker) (FIG. 5A). This strongly indicates that consistent exposure to mutagens give rise to elevated levels of CD8 $CD11a^{int}$ $CD82^{hi}$ T cells. FIG. 5B shows representative CD82/CD11a blots for smokers. FIG. 5C shows the only non-smoker in this analysis having a proportion of more than 3% CD8+ $CD11a^{int}$ $CD82^{hi}$ T cells.

Figure 6:
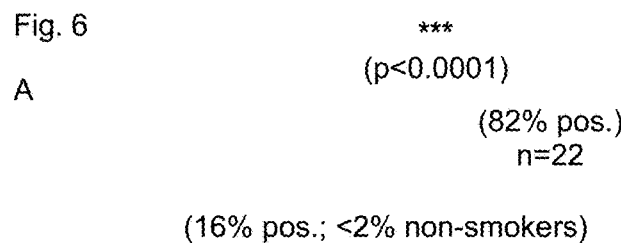
FIGS. 6A and 6B compare cancer patients (no CPI treatment) with voluntary donors (smokers and non-smokers) (A) with regard to CD82$^{hi}$CD11a$^{in}$CD8+ T cells (B).
Figure 6:
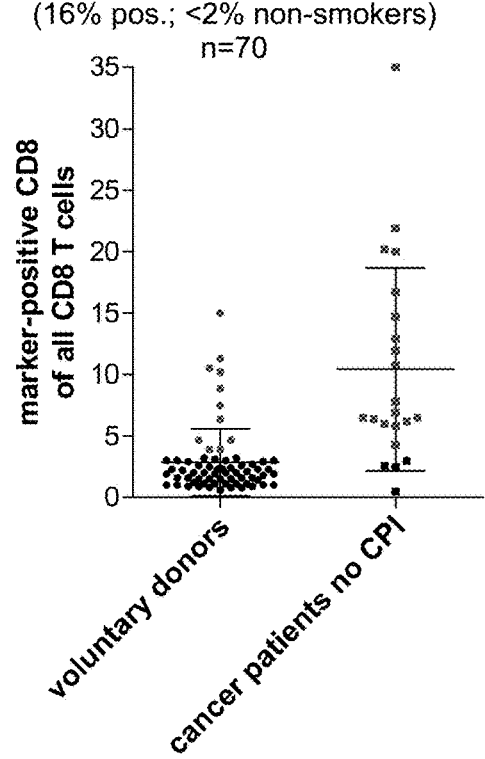
Figure 6:
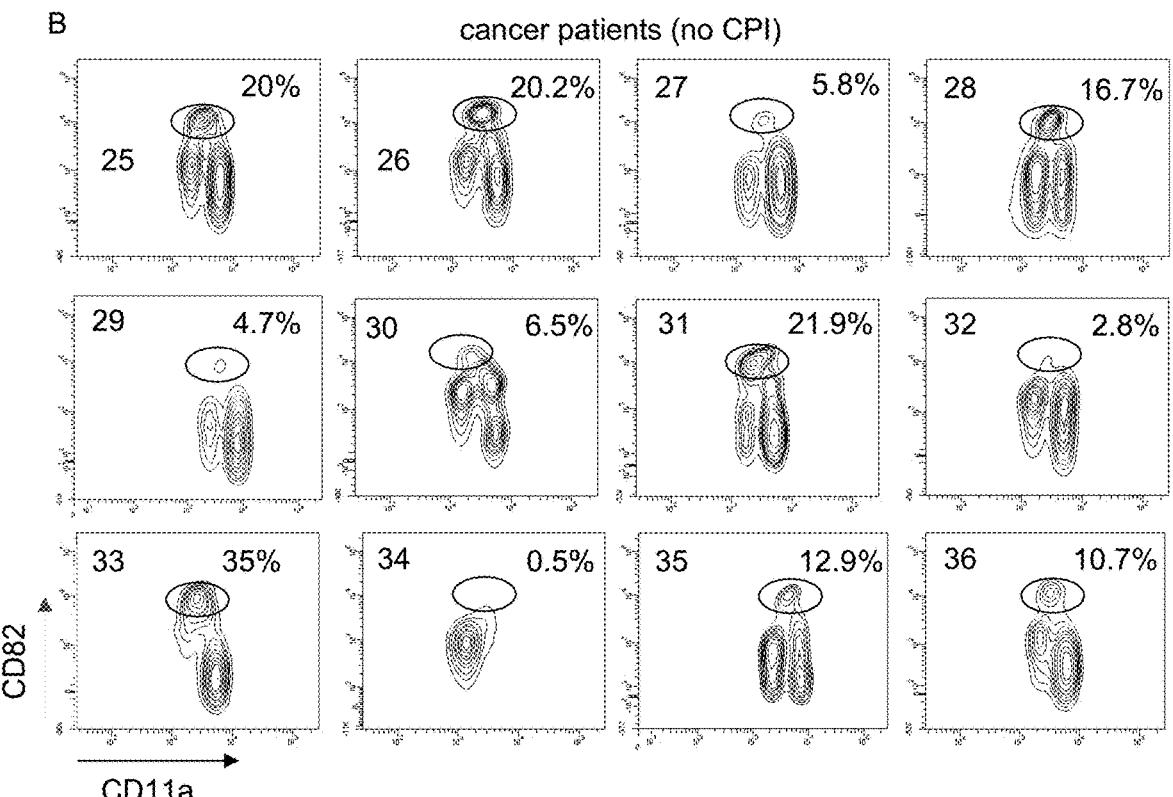

Next, blood from cancer patients was investigated to assess the frequency of CD8+ $CD11a^{int}$ $CD82^{hi}$ T cells. These experiments were in accordance with the ethical guidelines of Hannover medical school. Patients, mainly suffering from hepatocellular carcinoma (HCC), donated a blood sample prior to treatment with checkpoint inhibitors (CPI) nivolumab or pembrolizumab (FIGS. 6A and B).

Figure 7:
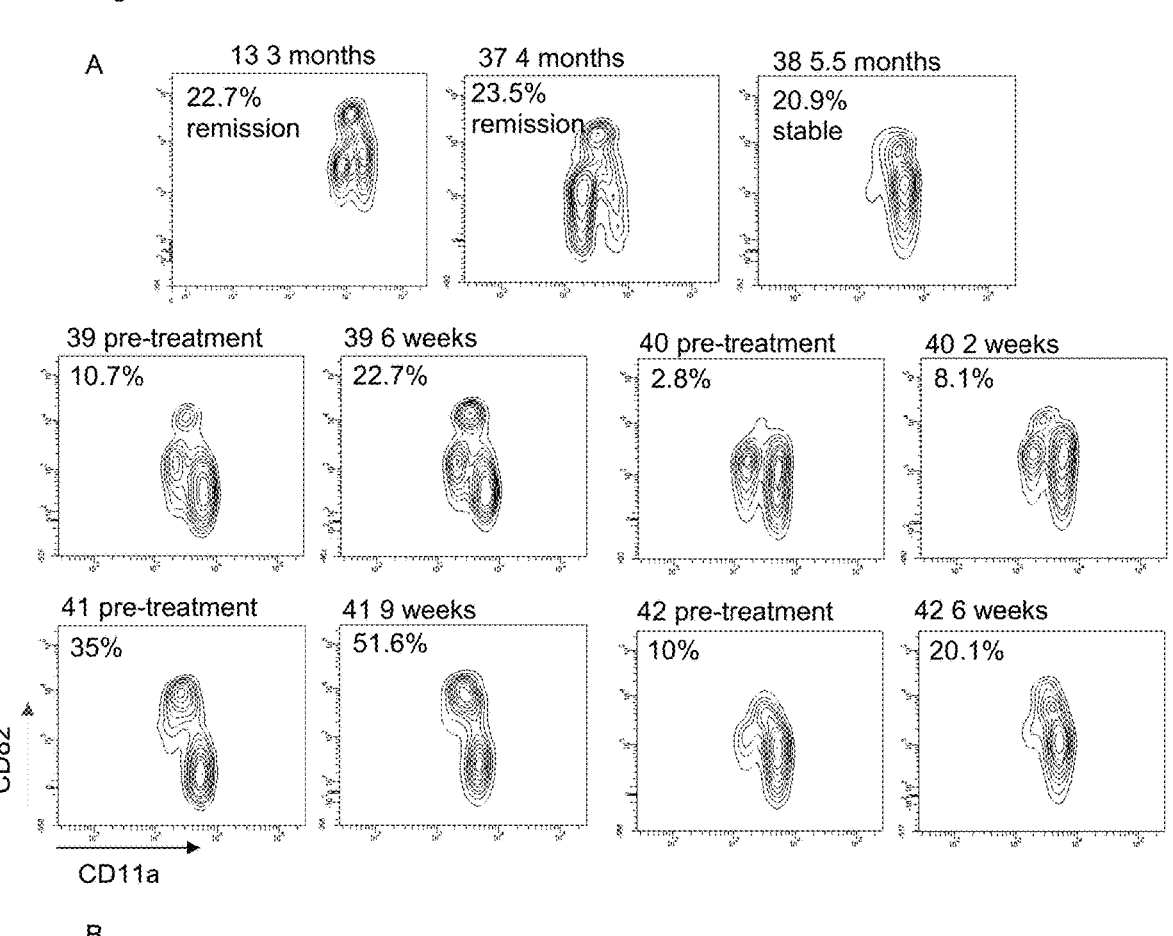
FIG. 7 shows an increase in CD82$^{hi}$CD11a$^{in}$CD8+ T cells in cancer patients before and under CPI treatment, wherein the patients respond to said treatment (over plots: patient number+time of analysis relative to CPI treatment) (A). B shows the increase in marker-positive (CD82$^{hi}$CD11a$^{in}$CD8+) T cells, wherein the peak numbers of these cells after treatment assessed before staging (i.e., before CT assessment of tumor size) are compared to pre-treatment levels, for 10 liver cancer patients under CPI treatment. CPI treatment was second or third line treatment. As first line treatment, most patients had been treated with sorafenib. CPI treatment was with nivolumab (patients treated every 2 weeks) or with pembrolizumab (patients treated every 3 weeks). Patients are grouped for their response to treatment (NR=non-responder, MR=mixed response, SD=stable disease, R=responder (as found in CT, grouped according to response evaluation criteria in solid tumors (RECIST)). Only one patient was a responder, i.e., in this patient group, the overall response rate was 10%. This patient had an increase in marker-posive cells of more than 12%, in particular, 16.6%.
Figure 7:
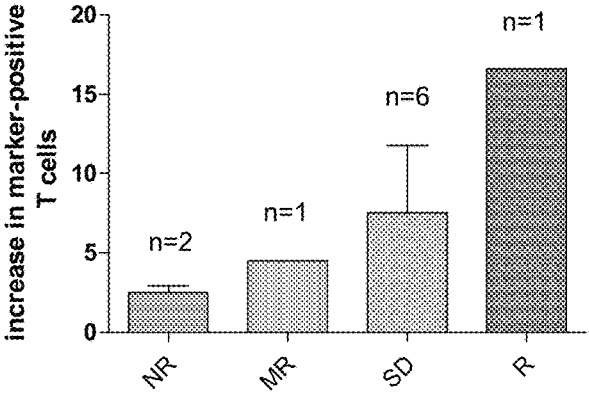

Representative samples of patients treated with CPI are shown in FIG. 7A. Of three responding cancer patients (13, 37, 38) samples were unavailable prior to treatment. High levels of putatively cancer-specific T cells (based on the CD8+$CD11a^{int}$ $CD82^{hi}$ phenotype) were detectable in these patients. Patients 39 to 42 show an expansion of CD8 $CD11a^{int}$ $CD82^{hi}$ T cells following immunotherapy within a time frame of two to nine weeks. These results demonstrate that checkpoint inhibition leads to an expansion of these cells in cancer patients. The graph in FIG. 7B depicts the changes of tumor-specific CD8 T cells between prior to therapy and the highest value of a measurement in a temporal vicinity of the first staging during therapy, which was usually about 12 weeks. Results of 10 patients were available. The ORR in this study is 10%.

Figure 8:
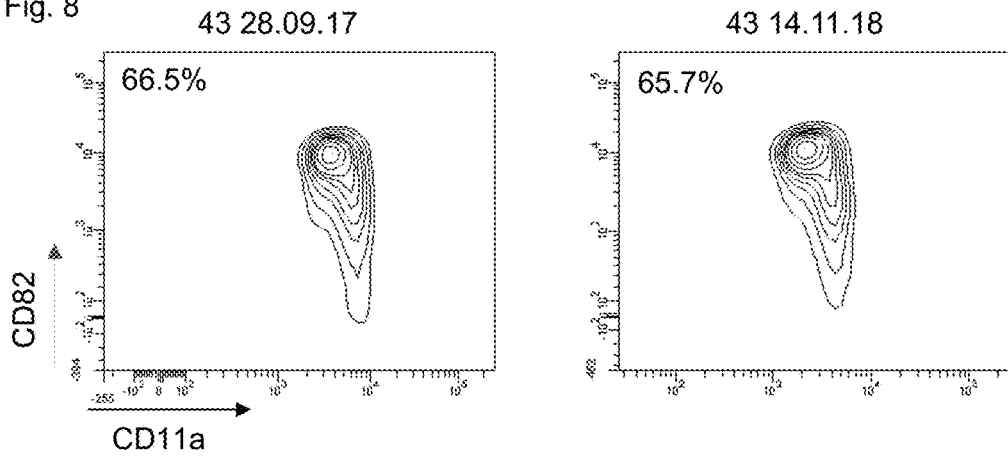
FIG. 8 shows the high frequency of CD82$^{hi}$CD11a$^{in}$CD8+ T cells in a 83 year old patient (Patient 43) which is shown to be stable over more than a year. The patient has an exceptional long survival time nearly 20 years post HCC diagnosis, as described in detail below.

FIG. 8 illustrates the tumor-specific T cell measurement of an extraordinary case report of an 83 year old patient with an exceptional history of HCC. The median overall survival time of 518 untreated HCC patients was 3.6 months and survival times were 13.4, 9.5, 3.4, and 1.6 months for patients of Barcelona Clinic Liver Cancer stages 0/A, B, C, and D, respectively. (Khalaf et al., Clinical Gastroenterology and Hepatology 2017; 15:273-2). HCC has a 5-year survival rate of 18%. Unresectable HCC remains an incurable disease (Chen et al., Oncology Letters 15: 855-862, 2018)

The present patient was diagnosed in the year 2000 with HCC. The tumor was resected four month later. He left the clinic and returned almost seven years later with a relapse. This is very uncommon, since the 5-year survival rate of HCC is only 18%. The tumor was then treated with transarterial chemoembolization. Additionally, he was also enrolled into a study for a treatment with a peptide vaccine, which turned out to be negative. Again, close to seven years later he showed up with a relapse. The single tumor that progressed in the meantime was then treated with RFA (radiofrequency ablation, i.e. local boiling of tumor tissue with electromagnetic radiation). Two years later he had another relapse that was treated likewise. At that time point the first blood sample was available. One year later, the follow up identified small HCC lesions (time point of second blood sample). This patient is still alive and now approaches his $20^{th}$ year post HCC diagnosis. Among oncologists, this has been described as a unique case.

The frequency of CD8+$CD11a^{int}$ $CD82^{hi}$ T cells in the sample of this patient was found to be >65%, and it was stable over the period of one year between both blood withdrawals (FIG. 8). This result strongly correlates with the unusual survival of the patient and the high frequency of the putative cancer-specific T cells.

Figure 9A:
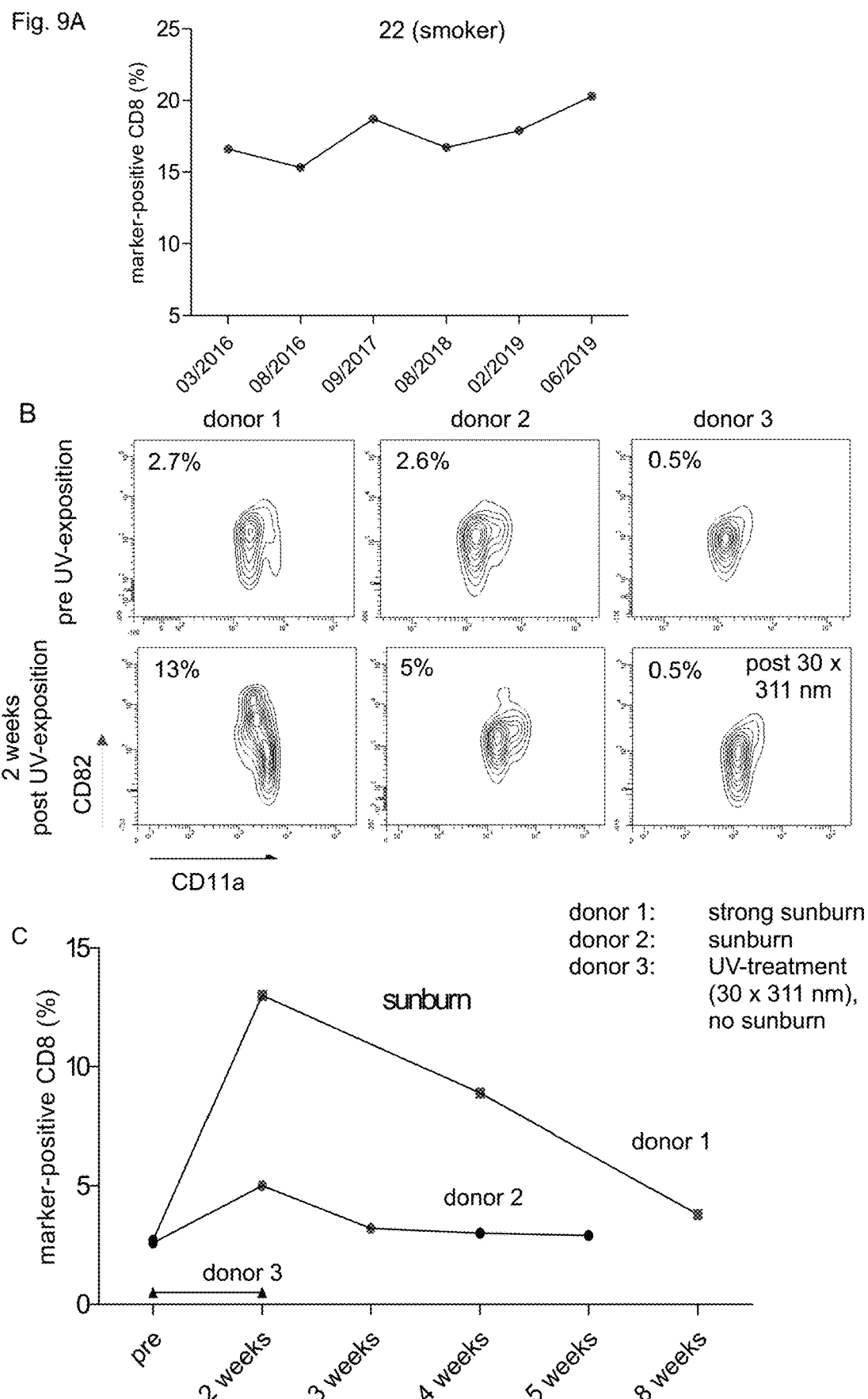
FIG. 9A shows the relative stability of the high frequencies of CD82$^{hi}$CD11a$^{int}$CD8+ T cells seen in a smoker. In contrast, increased numbers of CD82$^{hi}$CD11a$^{int}$CD8+ T cells due to a dermatitis solaris rapidly contracted (FIG. 9B, C). UV-treatment in the absence of sunburn did not increase the level of CD82$^{hi}$CD11a$^{int}$CD8+ T cells.

As described above, smokers have a higher rate of occurrence of CD8+ CD11a$^{int}$ CD82$^{hi}$ T cells. In one case it was possible to follow up this frequency throughout an extended period of time. Smoker 22, the volunteer with the highest rate of putative cancer-specific T cells, had a stable pool of these cells in a time frame of over three years (FIG. 9A). In contrast, two donors (donor 1 and 2) of the control arm of this study suffered a dermatitis solaris after extended sun exposure in Australia. Two weeks after this event, a blood sample was obtained and increased levels of CD8+ CD11a$^{int}$ CD82$^{hi}$ T cells were detected. Moreover, intensity of the sunburn correlated with the mutation-related T cell magnitude. Within a matter of weeks, these cells contracted and went back to normal levels.

Donor 3, a 9 year old girl, served as a control. This donor suffers a very rare pediatric disease of CD8 mycosis fungoides, a cutaneous T cell lymphoma that is treated with 311 nm narrow band UV radiation. The second sample of donor 3 was obtained immediately after 30 treatments of UV irradiation. As shown in FIG. 9B, UV treatment per se does not induce CD8 CD11a$^{int}$ CD82$^{hi}$ T cells. Experienced dermatologists scrupulously took care by adjusting the UV intensity, that dermatitis solaris was avoided during treatment to prevent long term complications. Of note, donor 3 was not treated by a checkpoint inhibitor therapy.

Taken together, these results show that sunburn induces a CD8+ CD11a$^{int}$ CD82$^{hi}$ T cell pool that rapidly contracts within weeks. This is an indication that mutagenic events caused by increased UV exposure with resulting dermatitis solaris specifically may trigger this cell type.

Figure 10:
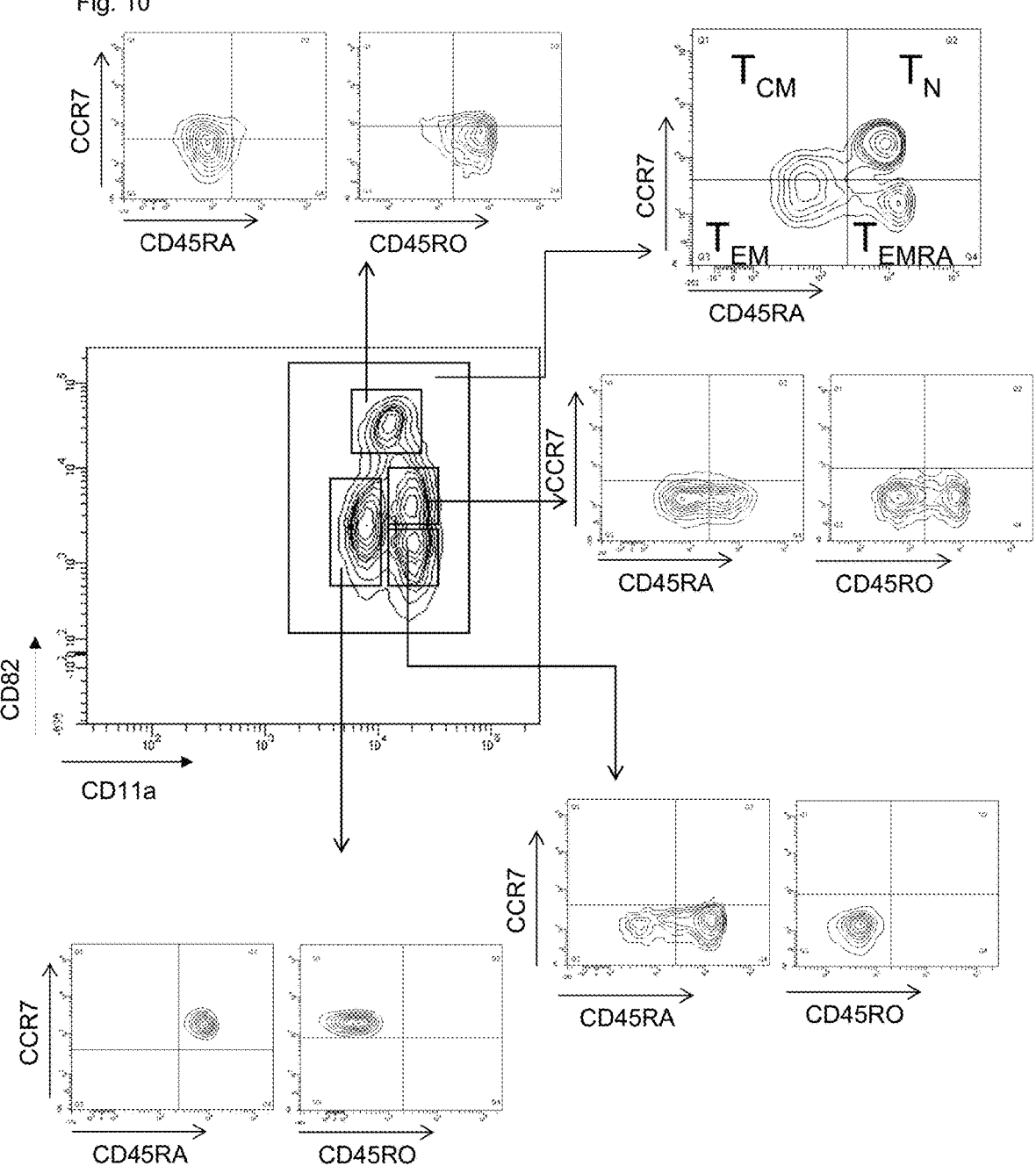
FIG. 10 shows an analysis of the memory phenotypes of CD8+ T cells in the CD11a/CD82 plots.

The memory phenotypes of CD8+ T cells in the CD11a/CD82 plots were investigated in FIG. 10. Expression levels of CD45RA and CCR7 are depicted in the upper right plot for all CD8 T cells. According to this analysis, T cells can be divided into naïve T cells (CD45RA+ CCR7+), central memory T cells (CD45RA− CCR7+), effector memory T cells (CD45RA− CCR7−), and effector memory RA+ T cells (CD45RA+ CCR7−). The source of this analysis is patient 13, and the results were validated in other patients and smokers. Expression of CD45RA and CD45RO are mutually exclusive, hence only one of these CD45 variants are expressed on the cell surface. CD8+ CD11a$^{lo}$ CD82$^{lo}$ T cells (lower left plot) express CD45RA+ CCR7+ and are thus naïve T cells by definition. CD8+ CD11a$^{hi}$ CD82$^{lo}$ split into two groups. In the central plot, these two groups can be distinguished as two separate populations. However, this resolution is not seen in every individual, as these populations mostly appear as one. However, the lower population is to a great extend CD45RA+ and thus CD45RO negative. With increasing CD82 expression levels, the count of CD45RA+ cells decreases in the upper population of CD8+ CD11a$^{hi}$ CD82$^{lo}$ cells. Cells with highest expression levels of CD82 in cancer patients (the CD8+ CD11a$^{int}$ CD82$^{hi}$ pool) are negative for CD45RA. CD45RA has been described as a marker that correlates with the absence of the corresponding antigen on memory cells [Rovaris et al., Blood 2006; 108(9):2897-905].

This is additional evidence that CD8+ CD11a$^{int}$ CD82$^{hi}$ T cells are cancer-specific cells, because continuous presence of a T cell antigen in a cancer patient inhibits, as evident in this study, development of CD45RA expression. As shown in FIG. 9, rapid CD8+ CD11a$^{int}$ CD82$^{hi}$ T cell contraction was observed in individuals with solaris dermatitis. Additionally, absence of CD8+ CD11a$^{int}$ CD82$^{hi}$ T cells was found in a triple negative breast cancer patient 8 weeks after complete tumor remission following nivolumab treatment (data not shown), which indicates that T cells may rapidly contract after complete clearance of target cells. Until today, this woman is under frequent follow-up with CT scans and still found to be tumor free. These results indicate that tumor-specific T cells may contract upon clearance of the antigen, instead of generating a memory pool. This has important implications for the development of this method for diagnostic purposes, as it decreases the risk of false positives due to a past tumor disease already cleared by the immune system.

Figure 11:
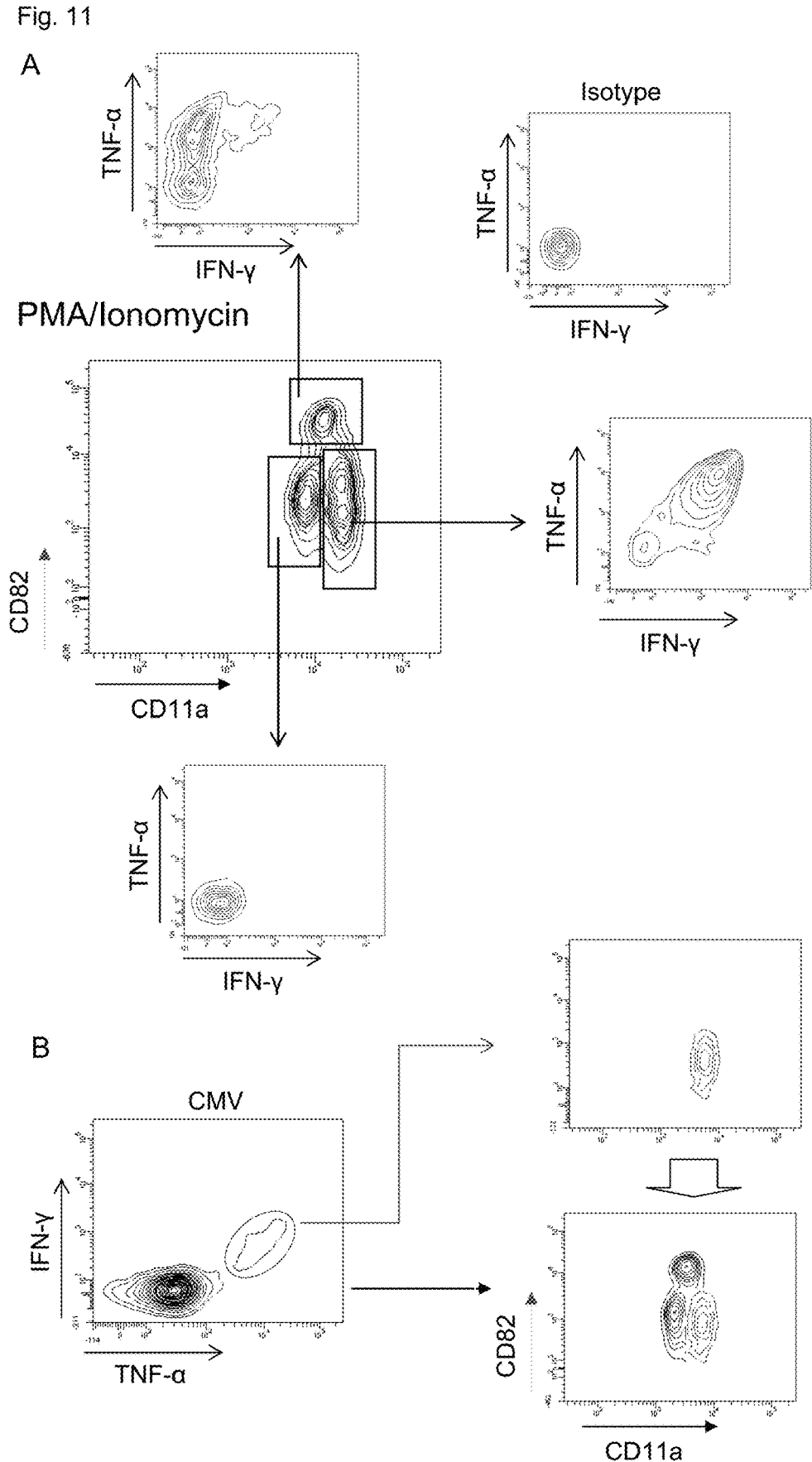
FIG. 11A shows that mutation-related T cells identified according to the method of the invention have a different phenotype with regard to cytokine secretion. CD8+ T cells activated with PMA/Ionomycin from a HCC patient could be separated into different groups. Naïve CD8+ T cells do not secrete tumor necrosis factor alpha (TNF-α) nor interferon gamma (IFN-γ). CD8+ CD11a$^{hi}$ CD82$^{lo}$ cells stain double positive in the intracellular cytokine staining for IFN-γ and TNF-α, whereas CD8 CD11a$^{int}$ CD82$^{hi}$ T cells are mostly TNF-α positive or double negative and secrete very little IFN-γ.

Activating CD8+ T cells with PMA and Ionomycin leads to a general activation and cytokine secretion in an antigen-independent manner. Activating CD8+ T cells from a responding cancer patient allows for assessment of the cytokine profile of all three populations described above. FIG. 11 demonstrates that naïve CD8+T cells, as expected, do not secrete tumor necrosis factor alpha (TNF-α) nor interferon gamma (IFN-γ). CD8+ CD11a$^{hi}$ CD82$^{lo}$ cells stain double positive in the intracellular cytokine staining for IFN-γ and TNF-α, whereas CD8 CD11a$^{int}$ CD82$^{hi}$ T cells are mostly TNF-α positive or double negative and secrete very little IFN-γ. This analysis show that CD8+ CD11a$^{hi}$ CD82$^{lo}$ and CD8 CD11a$^{int}$ CD82$^{hi}$ T cells differ greatly in their cytokine secretion profile (FIG. 11A).

In an antigen-specific approach, a HLA-A2+ HCC patient showed a positive cytokine response to CMV (cytomegalovirus) (FIG. 11B). CD8+ T cells were gated for IFN-γ and TNF-α (left blot) and then analyzed for CD11a and CD82 (right top blot). As shown by the comparison with the CD8+ T cells not gated for cytokine production (right bottom blot), the virus-specific cells producing both IFN-γ and TNF-α were only located in the CD8 CD11a$^{hi}$ CD82$^{lo}$ section and not in the CD8 CD11a$^{int}$ CD82$^{hi}$ area. Hence, virus-specific CD8 T cells are excluded from the tumor-specific area in this experiment. This is further evidence that CD8 CD11a$^{int}$ CD82$^{hi}$ T cells account for tumor-specificity.

The plots of an HCC patient depicted in FIG. 12. It shows a case of hyperprogressive disease. Prior to CPI, an amount of about 16% of tumor-specific CD8 T cells were detectable. Upon treatment start, that pool contracted rapidly within the following weeks. She died prior to the 6$^{th}$ treatment week. In case of a contraction of the pool of tumor-specific CD8+ T cells under CPI therapy, the CPI treatment should be discontinued. If possible, tumor-specific T cells, preferably, isolated from the patient before start of the CPI treatment and cultivated in vitro may be useful in adoptive T cell therapy of such patients.

4. Analysis of Further Surface Markers for Mutation-Related Human CD8+ T Cells

In a further screen, as shown in FIG. 13, CD194 (ab clone L291H4) was identified as an alternative or additional marker for mutation-related human T cells. Further, FIG. 14 shows that CD11a and CD18 (ab clone TS1/18) are substantially co-expressed, so that any of them can be used as an additional marker for mutation-related human T cells in combination with CD82 and/or CD194.

Further screening identified CD244 (ab clone C1.7), CD28 (ab clone CD28.2), CD62L (ab clone DEREG-56) and CD55 (ab clone JS11) as an alternative or additional marker for mutation-related human T cells. Additionally, CD43$^{int}$ expression (ab clone CD43-10G7) was found to be an additional or alternative marker for mutation-related T cells, similar to CD11 or CD18 expression (FIG. 15).

The invention claimed is:

1. A method for providing human mutation-related CD8+ T cells, comprising
    a) assaying CD8+ T cells from a subject for expression of CD82, wherein CD82$^{hi}$ cells are identified as mutation-related CD8+ T cells, and
    b) purifying the mutation-related CD8+ T cells.

2. The method of claim 1, further comprising analysing the expression of a marker selected from a group consisting of CD11a, CD18 and CD43 of the CD8+ T cells, wherein cells identified as mutation-related CD8+ T cells according to CD82 expression that are further CD11a$^{int}$, CD18$^{int}$, and/or CD43$^{int}$ are identified as mutation-related CD8+ T cells.

3. The method of claim 2, comprising analysing the expression of CD11a of the CD8+ T cells, wherein CD82$^{hi}$CD11a$^{int}$ cells are identified as mutation-related CD8+ T cells.

4. The method of claim 2, wherein cells that are both CD18$^{int}$ cells and CD82$^{hi}$ cells are identified as mutation-related CD8+ T cells.

5. The method of claim 2, wherein cells that are both CD43$^{int}$, cells and CD82$^{hi}$ cells are identified as mutation-related CD8+ T cells.

6. The method of claim 1, wherein the mutation-related CD8+ T cells are selected from the group consisting of tumor-specific CD8+ T cells, smoking-related CD8+ T cells, and or sunburn-related CD8+ T cells.

7. The method of claim 1, wherein the subject is not a smoker and not a sunburned subject, wherein the mutation-related CD8+ T cells are identified as tumor-specific CD8+ T cells.

8. The method of claim 1, wherein the method comprises contacting the CD8+ T cells with antibodies to CD82.

9. The method of claim 8, wherein the method comprises contacting cells with antibodies to CD11a, CD18 and CD43.

10. The method of claim 8, wherein the antibodies are labelled, and wherein the method comprises flow cytometry.

11. The method of claim 1, comprising providing a composition comprising at least 90% of CD82$^{hi}$ mutation-related human CD8+ T cells purified using the method of claim 1.

12. The method of claim 1 further comprising activating the mutation-related CD8+T cells.

13. The method of claim 1, comprising assaying the CD8+ T cells for the expression of CD244, wherein CD244− cells are identified as mutation-related CD8+ T cells.

14. The method of claim 1, wherein the CD8+ T cells are obtained from a blood sample from the subject.

15. A composition comprising at least 90% of human mutation-related CD8+ T cells that are a) CD8+ and b) CD82$^{hi}$ and c) CD11a$^{int}$ and/or CD18$^{int}$ and/or CD43$^{int}$.

16. A method of isolating any tumor-specific human CD8+ T cell clone, comprising carrying out the method of claim 11.

* * * * *